US009381252B2

(12) United States Patent
Agüeros Bazo et al.

(10) Patent No.: US 9,381,252 B2
(45) Date of Patent: Jul. 5, 2016

(54) NANOPARTICLES FOR ENCAPSULATION OF COMPOUNDS, THE PRODUCTION AND USES THEREOF

(75) Inventors: Maite Agüeros Bazo, Pamplona-Navarra (ES); Irene Esparza Catalán, Pamplona-Navarra (ES); Carolina González-Ferrero, San Adrián-Navarra (ES); Carlos Javier González Navarro, San Adrián-Navarra (ES); Juan Manuel Irache Garreta, Pamplona-Navarra (ES); Ana Romo Hualde, San Adrián-Navarra (ES)

(73) Assignee: UNIVERSIDAD DE NAVARRA, Pamplona (Navarra) (ES)

( * ) Notice: Subject to any disclaimer, the term of this patent is extended or adjusted under 35 U.S.C. 154(b) by 128 days.

(21) Appl. No.: 13/809,089

(22) PCT Filed: Jul. 15, 2011

(86) PCT No.: PCT/ES2011/070518
§ 371 (c)(1),
(2), (4) Date: Jan. 8, 2013

(87) PCT Pub. No.: WO2012/007628
PCT Pub. Date: Jan. 19, 2012

(65) Prior Publication Data
US 2013/0116261 A1    May 9, 2013

(30) Foreign Application Priority Data
Jul. 16, 2010   (ES) .................................. 201031095

(51) Int. Cl.
*A61K 8/44*  (2006.01)
*A61K 47/42* (2006.01)
(Continued)

(52) U.S. Cl.
CPC ............... *A61K 47/42* (2013.01); *A23L 1/0029* (2013.01); *A61K 8/11* (2013.01); *A61K 8/44* (2013.01);
(Continued)

(58) Field of Classification Search
None
See application file for complete search history.

(56) References Cited

U.S. PATENT DOCUMENTS 5,679,377 A * 10/1997 Bernstein et al. ............. 424/491
2007/0059340 A1  3/2007 Bello et al.
(Continued)

FOREIGN PATENT DOCUMENTS

CN   201092514 Y   7/2008
CN   101485629 A   7/2009
(Continued)

OTHER PUBLICATIONS

Rose et al. (JBC 1924;61:747-773).*
Patel et al. (J Agric Food Chem. 2010;58:12497-12503).*
Cserhati, T., et al.; "Effect of pH and salts on the binding of free amino acids to the corn protein zein studied by thin-layer chromatography," Amino Acids, 2005, pp. 99-103, vol. 28.
Fernandez, Avelina, et al., "Novel route to stabilization of bioactive antioxidants by encapsulation in electrospun fibers of zein prolamine," Food Hydrocolloids, 2009, pp. 1427-1432, vol. 23.
(Continued)

*Primary Examiner* — Ernst V Arnold
(74) *Attorney, Agent, or Firm* — Tristan A. Fuierer; Moore & Van Allen, PLLC

(57) ABSTRACT

The present invention relates to nanoparticles for the encapsulation of compounds, the obtaining and uses thereof. The nanoparticles comprise a zein matrix and a basic amino acid. The nanoparticles can encapsulate a water-soluble or fat-soluble biologically active compound. It is applicable in the food, pharmaceutical and cosmetic sectors and in the nanotechnology sector.

19 Claims, 6 Drawing Sheets

(51) Int. Cl.

| | | |
|---|---|---|
| *A61K 8/11* | (2006.01) | |
| *A61K 8/67* | (2006.01) | |
| *A61Q 19/00* | (2006.01) | |
| *B82Y 5/00* | (2011.01) | |
| *A23L 1/00* | (2006.01) | |
| *A61K 8/64* | (2006.01) | |
| *A61K 47/18* | (2006.01) | |
| *A61K 8/49* | (2006.01) | |

(52) U.S. Cl.
CPC ............... *A61K 8/498* (2013.01); *A61K 8/645* (2013.01); *A61K 8/67* (2013.01); *A61K 47/183* (2013.01); *A61Q 19/00* (2013.01); *A23V 2002/00* (2013.01); *A61K 2800/412* (2013.01); *B82Y 5/00* (2013.01); *Y10S 264/59* (2013.01)

(56) References Cited

U.S. PATENT DOCUMENTS

| | | | |
|---|---|---|---|
| 2008/0305096 A1* | 12/2008 | Verdegem et al. | ........... 424/94.4 |
| 2010/0285132 A1 | 11/2010 | Higbee et al. | |
| 2011/0064794 A1 | 3/2011 | Deng et al. | |
| 2014/0308351 A1 | 10/2014 | Perumal et al. | |

FOREIGN PATENT DOCUMENTS

| | | |
|---|---|---|
| JP | 2004269384 A | 9/2004 |
| JP | 2009518306 A | 5/2009 |
| WO | 2008157629 A1 | 12/2008 |
| WO | 2009137112 A1 | 11/2009 |

OTHER PUBLICATIONS

Li, Y, et al.; "Electrospun Zein Fibers as Carriers to Stabilize (−)-Epigallocatechin Gallate," Journal of Food Science, 2009, pp. C233-C240, vol. 74.

Muthuselvi, L., et al.; "Simple coacervates of zein to encapsulate Gitoxin," Colloids and Surfaces B:Biointerfaces, 2006, pp. 39-43, vol. 51.

Parris, Nicholas, et al.; "Encapsulation of Essential Oils in Zein Nanosphericai Particles," Journal of Agricultural and Food Chemistry, 2005, pp. 4788-4792, vol. 53.

Shukla, Rishi, et al.; "Zein : the industrial protein from Corn," Industrial Crops and Products, 2001, pp. 171-192, vol. 13.

Yoshimaru, Tetsuro, et al., "Microencapsulation of L-Lysine for Improving the Balance of Amino Acids in Ruminants," J. Fac. Agr. Kyushu Univ., 2000, pp. 359-365, vol. 44.

Zhong, Qixin, et al.; "Sustained release of lysozyme from zein microcapsules produced by a supercritical anti-solvent process," Food Chemistry, 2009, pp. 697-700, vol. 115.

Zhong, Qixin, et al.; "Zein nanoparticles produced by liquid-liquid dispersion," Food Hydrocolloids, 2009, pp. 2380-2387, vol. 23.

International Search Report, Nov. 23, 2011.

Singh, Amit, et al; "Nonospheres: A Novel Approach for Targeted Drug Delivery System," International Journal of Pharmaceutical Sciences Review and Research, 2010, pp. 84-88, vol. 5.

Soppimath, Kumaresh S., et al.; "Biodegradable polymeric nanoparticles as drug delivery devices," Journal of Controlled Release, 2001, pp. 1-20, vol. 70.

Irache, Juan M., et al; "Nanomedicine: Novel approaches in human and veterinary therapeutics," Veterinary Parasitology, 2011, pp. 47-71, vol. 180.

\* cited by examiner

A

B

NANOPARTICLES FOR ENCAPSULATION OF COMPOUNDS, THE PRODUCTION AND USES THEREOF

CROSS-REFERENCE TO RELATED APPLICATIONS

This application is filed under the provisions of 35 U.S.C. §371 and claims the priority of International Patent Application No. PCT/Es2011/070518 filed on 15 Jul. 2011 entitled "Nanoparticles for Encapsulation of Compounds, the Production and Uses Thereof" in the name of Maite AGÜEROS BAZO, et al., which claims priority to Spanish Patent Application No. P201031095, filed on 16 Jul. 2010, both of which are hereby incorporated by reference herein in their entirety.

FIELD OF THE INVENTION

The present invention is comprised in the food, pharmaceutical and cosmetic sectors and in the nanotechnology sector, and relates to the encapsulation of biologically active compounds using zein as a coating agent. The invention particularly relates to nanoparticles comprising a zein matrix and a basic amino acid, useful for encapsulating biologically active compounds, as well as the obtaining and applications thereof.

BACKGROUND OF THE INVENTION

Industries, particularly, the food, cosmetic and pharmaceutical industries, need to evolve technologically in order to meet new consumer demands. Nanotechnology can provide interesting solutions for said industries.

In particular, nanotechnology has a great potential for revolutionizing the food, cosmetic and pharmaceutical industries, since it allows encapsulating biologically active compounds [BACs], e.g., essential oils, antioxidants, minerals, prebiotics, flavors, vitamins, etc., for the purpose of obtaining various benefits, for example, increasing the useful life of the product, reducing the amount of BACs to be used, controlling the release thereof, increasing the bioavailability thereof, masking unwanted tastes, etc.

Antioxidants, substances which are capable of generating a benefit for the health of the consumer, form a group of BACs the use of which arouses an increasingly greater interest. The encapsulation of said antioxidant compounds, e.g., quercetin or resveratrol, in particular systems (e.g., microparticles or nanoparticles), for the purpose of protecting them and keeping them stable during their storage, is a very interesting option.

To date, the application of encapsulated antioxidant compounds is generally limited to the cosmetic and pharmaceutical fields. By way of illustration, the encapsulation of quercetin in (i) nanocapsules formed by poly-lactic-co-glycolic acid (PLGA) and ethyl acetate (Ghosh et al., *Life Sciences* 2009; 84:75-80), (ii) nanoparticles formed by Eudragit® [poly(meth)acrylates] and polyvinyl alcohol (Wu et al., *Int J of Pharm* 2008; 346:160-168), and (iii) in lipid microparticles formed with phosphatidylcholine and tristearin (Sccalia and Mezzena, *J Pharm Biomed Anal* 2009; 49:90-94) has been described. Likewise, the encapsulation of resveratrol in (i) polycaprolactone nanoparticles (Lu et al., *Int J of Pharm* 2009; 375:89-96), (ii) pectin microparticles (Das and Ng, *Int J of Pharm* 2010; 385:20-28), (iii) liposomes (Caddeo et al., *Int J of Pharm* 2008; 363:183-191), (iv) chitosan microspheres (Peng et al., *Food Chem* 2010; 121(1):23-28) and (v) polystyrene microspheres (Nam et al., *Polymer* 2005; 46:8956-8963) has been described.

However, the application of encapsulated antioxidant compounds in the food field is very limited since the materials used to encapsulate said compounds have toxicity problems or are not approved for use in foods. Likewise, the use of antioxidant compounds in the design of functional foods is very limited due to, among other reasons, their short half-life, high liability and low oral bioavailability. The encapsulation of antioxidant compounds, such as quercetin or resveratrol, to protect them in the food and to keep them stable during their entire storage period, furthermore allowing a controlled release which increases their bioavailability in the organism would be very desirable.

As is known, when designing a carrier suitable for encapsulating a BAC it is very important to correctly select the material used as the coating agent of matrix; to that end, the dosage form, its toxicity, the product in which the formulation is to be incorporated, etc., must be taken into account among other factors.

In the food nanotechnology field, it is not recommendable to use synthetic polymers since they can have toxicity problems. Although natural polymers do not have those drawbacks, their use requires developing more complicated methods for producing particles and, furthermore, in most cases, the particle size obtained (usually greater than 100 µm) is difficult to control, therefore such microparticles can be perceived by the consumer and alter the organoleptic characteristics of the target food.

The use of proteins, both of an animal origin, e.g., casein, albumin, etc., and of a plant origin, e.g., prolamines, etc. (ES 2269715, US 2004/86595, U.S. Pat. No. 5,679,377), as BAC coating agents, has been described.

Zein is the main storage protein present in the corn grain seed. It is a globular protein belonging to the prolamine group since it tends to have a large number of proline and glutamine amino acids and is characterized by its high insolubility in water. In recent years, this protein has become very important in the scientific and industrial field due to its particular physicochemical properties and to its molecular structure since it has amphiphilic characteristics and can form different self-assembled structures according to the hydrophilic-lipophilic compounds present in the medium (Wang et al., *Food Biophysics* 2008; 3:174-181). Therefore, zein offers a number of potential advantages as a raw material of films, since it is capable of forming hard and hydrophobic coatings with excellent flexibility and compressibility characteristics which are furthermore resistant to microbial attack.

As a result of these properties, new applications have bee found for zein as a an adhesive, biodegradable plastic, chewing gum, coating for food products, fiber, cosmetic powders, microencapsulator for pesticides and inks, etc. (Muthuselvi and Dhathathreyan, *Colloids and Surfaces B: Biointerfaces* 2006; 51:39-43). This protein is also used by the pharmaceutical industry to coat capsules for the purpose of protecting, releasing in a controlled manner and masking unwanted tastes and aromas (Shukla and Cheryan, *Industrial Crops and Products* 2001; 13:171-192). Furthermore, it has been proposed for the microencapsulation of insulin, heparin, ivermectin and gitoxin. Stable microparticles/microspheres, even in high humidity and heat conditions, which are furthermore resistant to bacterial attack are generally achieved (U.S. Pat. No. 5,679,377).

However, the use of zein as an encapsulating agent in the food field for the design of functional foods with encapsulated ingredients is still incipient. Obtaining zein nanoparticles for encapsulating essential oils using the phase separation technique (Parris et al., *J Agric Food Chem* 2005; 53:4788-4792), as well as the encapsulation of omega-3 fatty acids in said protein by applying the fluid bed technique to protect them from oxidation and to mask their negative organoleptic characteristics when they are introduced in the foods of interest (MX2008003213), have been described. Furthermore, the encapsulation of lycopene and the polyphenol epigallocatechin gallate (EGCG) in zein fibers by means of the electrospinning technique (Fernandez et al., Food Hydrocolloids 2009; 23:1427-1432 and Li et al. *J Food Sci* 2009; 74 (3):C233-C240 respectively), lysozyme by means of the SAS (supercritical anti-solvent) process (Zhong et al. *Food Chemistry* 2009; 115(2):697-700) and fish oil by means of the liquid-liquid dispersion method (Zhong et al., *J Food Process Pres* 2009; 33(2):255-270) has recently been achieved. These works described manufacturing techniques which are relatively complex and difficult to scale for their application in industry, or are exclusively limited to the encapsulation of lipophilic compounds and are not suitable for the encapsulation of hydrophilic compounds.

It is therefore necessary to develop versatile systems for the encapsulation of biologically active compounds which overcome all or part of the aforementioned drawbacks, which are suitable for carrying both water-soluble and fat-soluble compounds and, in particular, compounds the administration of which by other means entails difficulties, as is the case of antioxidant compounds. Additionally, it would also be highly desirable for said systems to be obtainable in a simple manner and to have a suitable stability during their storage and after their administration, which would facilitate their application in different technological sectors, e.g., the food, pharmaceutical and cosmetic sectors.

SUMMARY OF THE INVENTION

It has now been surprisingly found that the coating of both water-soluble and fat-soluble biologically active compounds (BACs) with a zein matrix and a basic amino acid provides nanoparticles which form a new system for encapsulating and stabilizing said BACs for their application in food, in cosmetic and in pharmacy.

Various tests performed by the inventors have shown that the addition of a basic amino acid together with zein facilitates the process for producing said nanoparticles comprising a zein matrix and a basic amino acid due to the fact that it enables using hydroalcoholic solutions with a relatively low percentage of alcohol to dissolve the zein, which in turn enables encapsulating both fat-soluble and water-soluble BACs. Furthermore, the use of basic additives or solvents which can cause toxicity problems is prevented, therefore the nutritional properties of the nanoparticles are improved. Likewise, the basic amino acid confers stability to the nanoparticles since the surface charge of the particles is increased, preventing the latter from aggregating.

Therefore, in one aspect, the invention relates to nanoparticles comprising a zein matrix and a basic amino acid. Said nanoparticles can be used to encapsulate water-soluble or fat-soluble BACs. In a particularly preferred embodiment, the BAC is an antioxidant compound. Furthermore, said nanoparticles can be used as technological additives [the encapsulated additive can be incorporated in matrices in which it is not soluble, favoring a uniform dispersion in the medium; by way of illustration, according to the invention, a fat-soluble BAC encapsulated in said nanoparticles can be dispersed in an aqueous matrix, a process which would have been complex if the BAC were in its free form (without being encapsulated)].

Said nanoparticles are stable and capable of protecting the BAC from its degradation by external agents, e.g., light, pH changes, oxidation, etc., both during the processing of the product (e.g., food, pharmaceutical or cosmetic product) and during its storage. Furthermore, when said nanoparticles are orally administered (e.g., food), they protect the BAC from the acidic conditions of the stomach and release the BAC in the desired place, for example, in the intestine.

In another aspect, the invention relates to a process for producing said empty nanoparticles, i.e., without BACs.

In another aspect, the invention relates to a process for producing said nanoparticles loaded with a BAC, such as a fat-soluble BAC or a water-soluble BAC.

Said processes are simple and applicable at industrial scale and advantageously do not include the use of synthetic polymers or reagents which are not approved as food additives, they allow minimizing the inclusion of surfactants or emulsifiers and they further allow obtaining nanoparticles of a nanometric scale, with a controllable particle size.

In a particular embodiment, said processes further comprise an additional step of drying the suspension containing said nanoparticles for the purpose of obtaining a formulation in powder form, which allows keeping the BAC stable over time; the formulations in powder form are particularly suitable for use in solid foods. The drying of said nanoparticles is advantageously carried out in the presence of a protective agent for the nanoparticles. The nanoparticles containing a BAC thus obtained can be easily resuspended in an aqueous medium, protecting the BAC from its degradation in solution. The final product obtained is stable and protects the BAC during long storage periods and is furthermore applicable to different types of foods, both liquid foods (e.g., beverages) and solid foods.

In another aspect, the invention relates to a composition comprising said nanoparticles for use in the food, pharmaceutical or cosmetic sectors. In fact, said nanoparticles can be incorporated in creams, gels and hydrogels for the purpose of obtaining stable cosmetic or pharmaceutical preparations suitable for use in those sectors. Said nanoparticles can likewise be formulated with excipients suitable for their topical administration.

In another aspect, the invention relates to a food product comprising said composition based on zein nanoparticles provided by this invention. In a particular embodiment, said food product is in liquid, semi-solid or solid form.

DETAILED DESCRIPTION OF THE INVENTION

Figure 1:
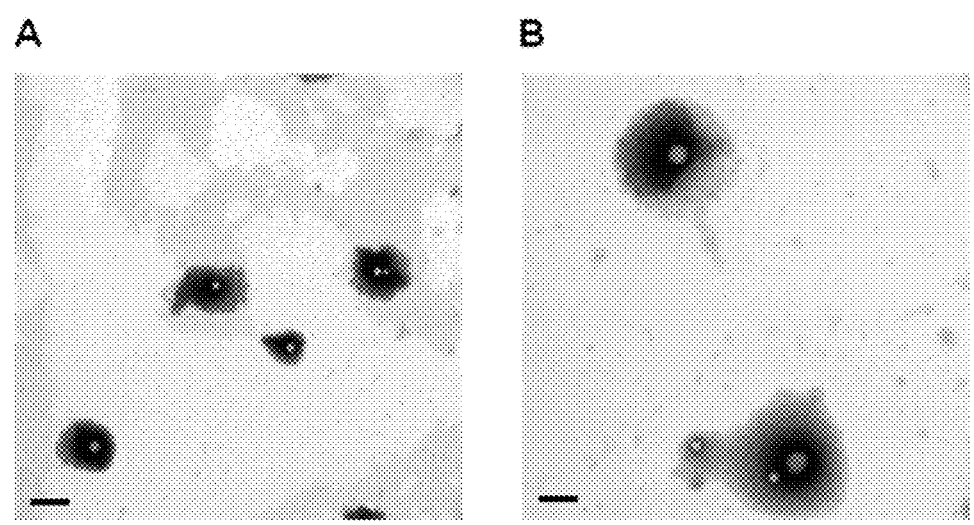
FIG. 1 shows the transmission electron microscopy (TEM) images of empty zein nanoparticles. A) 8,000× (the black bar located in the bottom left margin of the images corresponds to a reference of 200 nm). B) 15,750× (the black bar located in the bottom left margin of the images corresponds to a reference of 100 nm).

The present invention provides nanoparticles comprising a zein matrix and a basic amino acid and methods for encapsulating biologically active compounds (BACs) for the purpose of preserving them from the degradation by external agents (e.g., light, pH, oxidation, etc.). Said nanoparticles can be designed to allow a controlled release of the BAC for the purpose of increasing its bioavailability; the bioavailability can be increased by two routes: by means of the integral release of the encapsulated BAC in the intestine (its degradation minimized at the origin, in the food matrix and/or by storage as well as by the protection offered against the acidic conditions of the stomach) and by means of an effect of release of the BAC in a controlled manner or sustained over time.

DEFINITIONS

To facilitate the understanding of the present invention, the meaning of several terms and expressions as they are used in this description is indicated below.

As used herein, a "basic amino acid" refers to an organic molecule containing an amino group (—NH$_2$) and a carboxyl group (—COOH) and positive charge; said basic amino acid is preferably a basic alpha-amino acid such as lysine, arginine and histidine.

As used herein "approximately" refers to a range of values close to a specified value, such as ±10% of a specified value. For example, "approximately 20" includes ±10% of 20, or from 18 to 22. Furthermore, regardless of whether or not the term "approximately" is specified, the person skilled in the art understands that any numerical value expressed herein encompasses a close range of values. Such variations of a specified value can result from the experimental errors during the corresponding measurement.

As used herein, a "biologically active compound" or "BAC" refers to a compound having a nutritional, therapeutic and/or cosmetic activity; said compound can be fat-soluble or water-soluble. Non-limiting illustrative examples of BACs according to the present invention include amino acids, antimicrobial agents, flavoring agents, preservatives, sweeteners, steroids, drugs, hormones, lipids, peptides, polynucleotides, polysaccharides, proteins, proteoglycans, flavors, vitamins, etc.

As used herein, a "water-soluble biologically active compound" or "water-soluble BAC" refers to a compound which has a nutritional, therapeutic and/or cosmetic activity and which is soluble (very soluble, freely soluble, soluble, sparingly soluble or slightly soluble) in an aqueous solution according to the criteria defined by the Royal Spanish Pharmacopoeia:

| Descriptive terms | Approximate volumes of solvent in milliliters (mL) per gram of solute, referred to a temperature comprised between 15° C. and 25° C. |
|---|---|
| Very soluble | Less than 1 |
| Freely soluble | from 1 to 10 |
| Soluble | from 10 to 30 |
| Sparingly soluble | from 30 to 100 |
| Slightly soluble | from 100 to 1,000 |
| Very slightly soluble | from 1,000 to 10,000 |
| Practically insoluble | greater than 10,000 |

Non-limiting illustrative examples of water-soluble BACs include vitamins, for example, vitamins of the B or C families, and their derivatives, salts or esters; hyaluronic acid, chondroitin sulfate, thioctic acid, their salts or esters, etc. In a particular embodiment, said water-soluble BAC is selected from the group consisting of folic acid, 4-aminobenzoic acid, niacin, pantothenic acid, thiamine monophosphate, thiamine pyrophosphate, thiamine triphosphate, ascorbic acid, pteroylpolyglutamic acids (folic acid derivatives: folate polyglutamates; polyglutamate folates), folinic acid, nicotinic acid, hyaluronic acid, thioctic acid (alpha-lipoic acid), p-coumaric acid, caffeic acid, their food-grade or pharmaceutically or cosmetically acceptable derivatives, esters or salts, and mixtures thereof.

As used herein, a "fat-soluble biologically active compound" or "fat-soluble BAC" refers to a compound which has a nutritional, therapeutic and/or cosmetic activity and which is soluble (very soluble, freely soluble, soluble, sparingly soluble or slightly soluble) in fats and oils, according to the criteria defined by the Royal Spanish Pharmacopoeia. Non-limiting illustrative examples of fat-soluble BACs include vitamins, for example, vitamins of A, D, E, K families and their derivatives, phospholipids, carotenoids (carotenes, lycopene, lutein, capsanthin, zeaxanthin etc.), omega-3 fatty acids (docosahexanoic acid (DHA), eicosapentanoic acid (EPA), etc.), phytostanols and phytosterols (sitosterol, campesterol, stigmasterol, etc.), polyphenols (quercetin, rutin, resveratrol, kaempferol, myricetin, isorhamnetin, etc.) and their derivatives.

A product is said to be a "food-grade" product when it is safe for use in human or animal food, according to the Codex Alimentarius of a country or of an organization, for example, of the Food and Agriculture Organization of the United Nations (FAO) or of World Health Organization (WHO); consequently, a "food-grade" product is a non-toxic product "suitable for use in food" so both expressions are synonymous and are used without distinction in this description.

As used herein, "aqueous medium" refers to a medium comprising water. In a particular embodiment, the aqueous medium essentially consists of water.

As used herein, "hydroalcoholic medium" refers to a medium comprising water and an alcohol, in variable relative ratios. In a particular embodiment, said hydroalcoholic medium comprises a solution of ethanol in water, in any relative ratio between said compounds.

As used herein, "nanoparticle" refers to colloidal systems of the type of spheres or similar shapes with a size less than 1 micrometer (μm), preferably of the order of 10 to 900 nanometers (nm).

As used herein, "average size" refers to the average diameter of the population of nanoparticles which move together in an aqueous medium. The average size of these systems can be measured by standard processes known by the person skilled in the art, and which are described, for example, in the experimental part (see below).

As used herein, the term "zein" includes any globular protein belonging to the group of prolamines; said protein is generally synthesized during the development of the endosperm (nutritive tissue formed in the embryo sac of seed plants and usually forms a food deposit for the embryo of the seeds of various angiosperm plants). Zein can be obtained from any suitable source, although it is preferably obtained from corn. Various methods and techniques for extracting zein from corn endosperm are known; commercial zein is generally extracted from corn gluten meal (US 2009/0258050).

The study of zein reveals an extreme variability at the genetic level and, therefore, a complex situation among the different proteins forming part of the group of proteins known as zeins. Native zein is actually a large and heterogeneous family of several groups of proteins which differ in their molecular size, solubility, and charge. More than twenty different zein have been estimated to exist. The analysis of zein extracts by means of high-performance liquid chromatography (HPLC), ion-exchange chromatography, gel exclusion chromatography, SDS-polyacrylamide gel electrophoresis (SDS-PAGE), isoelectric focusing (IEF), amino acid analysis, and DNA cloning techniques have led to a better understanding of zein proteins.

The analysis of the composition of the amino acids of zein reveals a large amount of leucine, alanine, glutamine, and phenylalanine; however, lysine and tryptophan are absent or, alternatively, are present in very small amounts. The high proportion of non-polar amino acid residues and the exceptional lack of ionic groups are responsible for the hydrophobic nature thereof and for the particular solubility thereof.

The protein bodies of zein are formed by three types of structurally different proteins: alpha-zein ($\alpha$-zein), gamma-zein ($\gamma$-zein) [which includes beta zein ($\beta$-zein)], and delta-zein ($\delta$-zein). Said proteins can be classified into four classes $\alpha$-zein, $\beta$-zein, $\gamma$-zein and $\delta$-zein) based on the differences in solubility and sequence.

Zein extracted without reducing agents forms a large multigene family of polypeptides referred to as $\alpha$-zein. $\alpha$-zeins, generally the most abundant fraction of native zein, contain about 40 amino acids in the amino terminus which precede a series of 9 or 10 repeated peptides of 20 amino acids. These repeats are believed to be $\alpha$-helices and wind the protein into a rod-shaped molecule.

The other fractions of zein ($\beta$-, $\gamma$-, and $\delta$-zein) must be extracted using alcohols solutions of alcohols containing reducing agents to break the disulfide bonds. By way of illustration, mercaptoethanol is used for laboratory extraction. $\beta$-, $\gamma$-, and $\delta$-zeins show no sequence homology with $\alpha$-zein.

$\gamma$-Zein is soluble in both aqueous and alcoholic solvents in reducing conditions. Each of the $\gamma$-zeins has a unique N-terminus sequence. By way of example, in the 50 kDa $\gamma$-zein, this region is 136 amino acids long and it is very rich in histidine. The 27 kDa $\gamma$-zein has a series of eight tandem repeats of a hexapeptide which produce 11 amino acids after the amino terminus. The first eight amino acids of the 16 kDa $\gamma$-zein protein are identical to those of the 27 kDa $\gamma$-zein, but the 16 kDa $\gamma$-zein has three degenerate versions of proline-rich repeats. $\gamma$-Zein normally represents between 10 and 15% of the total of the zeins.

$\beta$-Zein, which is related to $\gamma$-zein, includes a methionine-rich 17 kDa polypeptide and constitutes up to 10% of the total zein. Approximately the last 140 amino acids of $\beta$- and $\gamma$-zeins are 85% identical. $\beta$-Zein has no repetitive peptides and seems to mostly consist of $\beta$-sheets and turn conformation.

$\delta$-zein is a 10 kDa protein and is a minor fraction of zein. $\delta$-zeins are the most hydrophobic of the group, contain no repetitive peptides, and are exceptionally methionine- and cysteine-rich.

Zein has been considered as a "Generally Recognized as Safe" (GRAS) product by the Food and Drug Administration (United States) since 1985 [CAS (Chemical Abstract Service) number: 9010-66-6].

In the present invention, the source or the grade of zein is not limited to a single zein and, in fact, any zein can be used to put the present invention into practice. By way of illustration, the commercial zeins which can be used in the present invention include, but are not limited to, the zein supplied by Sigma-Aldrich (product number Z 3625); Wako Puras Chemical Industries (product numbers 261-00015, 264-01281 and 260-01283); Spectrum Chemical (product numbers 21131 and ZE105); ScienceLab units SLZ1150; SJZ Chem-Pharma Company (product name ZEIN (GLIDZIN); Arco Organics (catalog numbers 17931-0000, 17931-1000, and 17931-5000); and Freeman Industries, zein regular grade F4000, zein regular grade F4400, zein special grade F6000, etc. In a particular embodiment, the commercial zein supplied by Sigma-Aldrich (product number Z 3625), obtained from corn, is used.

As used herein, the term "zein" includes both native zein and modified zein. The term "modified zein" includes any zein having an amino acid sequence which is normally not naturally-occurring, but which behave similarly to authentic zeins and which are soluble in alcohol. Amino acid substitutions, especially those which do not substantially modify the hydrophobicity, may be introduced. By way of illustration, amino acid substitutions can be performed within the repeated sections, or a single amino acid can be substituted, and substitutions can also be performed in the segments connecting the domains of repeated sequences. Insertions and substitutions can also be introduced in the carboxyl terminus and the amino terminus of the zein molecule. Additionally, deletions can be performed in the amino acid sequence provided that the resulting protein is functionally equivalent to zein, i.e., that it maintains its properties.

Nanoparticles of the Invention

In one aspect, the invention relates to a nanoparticle, hereinafter nanoparticle of the invention, comprising a zein matrix and a basic amino acid.

Virtually any zein can form the matrix of the nanoparticle of the invention; nevertheless, in a particular embodiment, said zein is a zein from corn, such as the zein supplied by Sigma-Aldrich (product number Z 3625).

In a particular embodiment, said basic amino acid is selected from the group consisting of arginine, lysine, histidine, and mixtures thereof.

The nanoparticles of the invention can be used to encapsulate a biologically active compound (BAC). The nanoparticles of the invention can furthermore be used as technological additives, for example, facilitating the incorporation of a fat-soluble BAC in an aqueous matrix, etc.

Therefore, in another particular embodiment, the nanoparticle of the invention further comprises a BAC. Said BAC can be a water-soluble BAC or a fat-soluble BAC; in this case, the nanoparticle of the invention is occasionally identified in this description as "loaded nanoparticle of the invention" to differentiate it from other nanoparticles of the invention which do not contain BACs (occasionally identified as "empty nanoparticles of the invention").

In a particular embodiment, said BAC is a fat-soluble BAC. In a more particular embodiment, said fat-soluble BAC is selected from the group consisting of:
- a) a polyphenol;
- b) a vitamin of the family of vitamins A, D, E or K;
- c) a precursor or a derivative of a vitamin according to b);
- d) a phospholipid;
- e) a carotenoid;
- f) a fatty acid;
- g) a phytostanol or a phytosterol;
- h) a salt or an ester of any of the previous compounds a)-g); and
- i) combinations thereof.

In a more particular embodiment, said fat-soluble BAC is:
- i) a polyphenol such as for example, a flavonol (e.g., a catechin, an epicatechin, isorhamnetin, kaempferol, myricetin, quercetin, etc.); an anthocyanin (e.g., cyanidin, delphinidin, malvidin, peonidin, petunidin, etc.); a phytoalexin (e.g., resveratrol, etc.); hydroxytyrosol, etc.;
- ii) a fat-soluble vitamin such as for example, vitamin A and its derivatives (e.g., retinoic acid, retinal, retinol, etc.); vitamin E and its derivatives (e.g., a tocopherol, for example, alpha-tocopherol, etc., a tocotrienol, etc.); vitamin D and its derivatives (e.g., vitamin $D_1$, vitamin $D_2$ (ergocalciferol), vitamin $D_3$ (cholecalciferol), vitamin $D_4$ (22-dihydroergocalciferol), vitamin $D_5$ (sitocalciferol), etc.); vitamin K or phytomenadione and its derivatives (e.g., vitamin K1 (phylloquinone), vitamin K2 (menaquinone), menadione, etc.);
- iii) a carotenoid such as for example, a carotene (e.g., alpha-carotene, beta-carotene, cryptoxanthin, lycopene, etc.); a xanthophyll (e.g., astaxanthin, canthaxanthin, capsanthin, cryptoxanthin, flavoxanthin, lutein, rodoxanthin, rubixanthin, violaxanthin, zeaxanthin, etc.);
- iv) a fatty acid such as for example, an omega-3 fatty acid (e.g., α-linolenic acid (ALA), eicosapentaenoic acid (EPA), docosahexanoic acid (DHA), etc.; an omega-6 fatty acid (e.g., γ-linoleic acid, etc.); or
- v) a phytosterol or a phytostanol (e.g., brassicasterol, campesterol, ergosterol, stigmasterol, sitostanol, sitosterol, etc.).

In a specific embodiment, said fat-soluble BAC is selected from the group consisting of a flavonol (e.g., quercetin, etc.), an anthocyanin, a phytoalexin (e.g., resveratrol, etc.), hydroxytyrosol, retinoic acid, retinal, retinol, calciferol (ergocalciferol and colecalciferol), alpha-tocopherol, tocotrienol, phytomenadione, alpha-carotene, beta-carotene, lycopene, capsanthin, lutein, zeaxanthin, xanthophyll, EPA, DHA, linoleic acid, campesterol, stigmasterol, sitosterol, their food-grade or pharmaceutically or cosmetically acceptable derivatives, esters or salts, and mixtures thereof.

In a more specific embodiment, said fat-soluble BAC is selected from the group consisting of quercetin, resveratrol, their food-grade or pharmaceutically or cosmetically acceptable derivatives, esters or salts, and mixtures thereof.

In another particular embodiment, said BAC is a water-soluble BAC. In a more particular embodiment, said water-soluble BAC is:
- a) a vitamin of the family of vitamins B or C;
- b) a derivative of a vitamin according to a);
- c) a compound selected from hyaluronic acid, chondroitin sulfate and thioctic acid;
- d) a salt or an ester of any of the previous compounds a)-c); and
- e) combinations thereof.

In a specific embodiment, said water-soluble BAC is selected from the group consisting of folic acid, its food-grade or pharmaceutically or cosmetically acceptable esters or salts, and mixtures thereof.

The use of the nanoparticles of the invention as systems for encapsulating antioxidant compounds is a particular and preferred embodiment.

Process for Obtaining the Nanoparticles of the Invention

In another aspect, the invention relates to a process for producing nanoparticles comprising a zein matrix and a basic amino acid (nanoparticles of the invention), hereinafter "process [1] of the invention", which comprises:
- a) preparing a hydroalcoholic solution containing a zein and a basic amino acid; and
- b) adding water to the solution of step a).

The hydroalcoholic solution used in step a) of process [1] of the invention contains water and an alcohol, typically ethanol; in a particular embodiment, said hydroalcoholic solution comprises between 25% and 75% (w/v) of alcohol, preferably between 30% and 60%, more preferably approximately 50%.

The amount of zein which the hydroalcoholic solution formed in step a) of process [1] of the invention can contain can vary within a wide range; nevertheless, in a particular embodiment, the amount of zein contained in said hydroalcoholic solution is comprised between 0.1% and 10% (w/v), preferably between 0.2% and 2.5%, more preferably between 0.5% and 1%.

The amount of basic amino acid which said hydroalcoholic solution formed in step a) of process [1] of the invention can contain can vary within a wide range. Generally, said amount is usually expressed according to the amount of zein to be dissolved. Thus, although the ratio by weight between the basic amino acid and the zein [basic amino acid:zein] present in said hydroalcoholic solution generally depends on the type of BAC to be encapsulated and can vary extensively, in a particular embodiment, said basic amino acid:zein ratio by weight is comprised between 1:0.01 and 1:50, typically between 1:0.5 and 1:25, preferably between 1:1 and 1:20, more preferably between 1:5 and 1:15; in a specific embodiment, the basic amino acid:zein ratio by weight is approximately 1:6.

In step b) of process [1] of the invention, water is added in an amount sufficient for the formation of the nanoparticles of the invention. Although the amount of water to be added can vary within a wide range, in a particular embodiment, water is added in an amount sufficient for the final proportion of alcohol in the medium to be comprised between 10% and 60% (w/v), preferably between 15% and 30%, more preferably approximately 25%.

In another aspect, the invention relates to a process for producing nanoparticles comprising a zein matrix, a basic amino acid and a fat-soluble BAC (nanoparticles of the invention loaded with a fat-soluble BAC), hereinafter "process [2] of the invention", which comprises:
- a) preparing a hydroalcoholic solution (i) containing a zein and a basic amino acid;
- b) preparing an alcoholic solution comprising a fat-soluble BAC and diluting it with water to obtain a hydroalcoholic solution (ii) comprising a fat-soluble BAC;
- c) mixing said hydroalcoholic solution (i) containing a zein and a basic amino acid with said hydroalcoholic solution (ii) comprising a fat-soluble BAC; and
- d) adding water to the mixture resulting from step c).

The hydroalcoholic solution (i) containing a zein and a basic amino acid used in step a) of process [2] of the invention contains water and an alcohol, typically ethanol; in a particular embodiment, said hydroalcoholic solution comprises between 25% and 75% (w/v) alcohol, preferably between 30% and 60%, more preferably approximately 50%. Said hydroalcoholic solution (i) is prepared by mixing its components in the suitable amounts.

The amount of zein which said hydroalcoholic solution (i) containing a zein and a basic amino acid used in step a) of process [2] of the invention can contain can vary within a wide range; nevertheless, in a particular embodiment, the amount of zein contained in said hydroalcoholic solution (i) is comprised between 0.1% and 10% (w/v), preferably between 0.2% and 2.5%, more preferably between 0.5% and 1%.

The amount of basic amino acid which said hydroalcoholic solution (i) containing a zein and a basic amino acid used in step a) of process [2] of the invention can contain can vary within a wide range. Said amount will generally be expressed according to the amount of zein to be dissolved. Thus, although the ratio by weight between the basic amino acid and the zein [basic amino acid:zein] present in said hydroalcoholic solution (i) can vary extensively, in a particular embodiment, said basic amino acid:zein ratio by weight is comprised between 1:0.01 and 1:50, typically between 1:0.5 and 1:25, preferably between 1:1 and 1:20, more preferably between 1:5 and 1:15; in a specific embodiment, the basic amino acid:zein ratio by weight is 1:6 (when the BAC is resveratrol) and 1:11 (when the BAC is quercetin) approximately.

The hydroalcoholic solution (ii) comprising a fat-soluble BAC generated in step b) of process [2] of the invention can be obtained by dissolving or solubilizing said fat-soluble BAC in an alcohol (e.g., ethanol) and then diluting the alcoholic solution obtained with water. Therefore, said hydroalcoholic solution (ii) comprising a fat-soluble BAC generated in step b) of process [2] of the invention contains water and an alcohol, typically ethanol; in a particular embodiment, said hydroalcoholic solution (ii) comprises between 25% and 75% (w/v) alcohol, preferably between 30% and 65%, more preferably between 50 and 60%.

The amount of fat-soluble BAC which said hydroalcoholic solution (ii) can contain can vary within a wide range; nevertheless, in a particular embodiment, the amount of fat-soluble BAC contained in said hydroalcoholic solution (ii) is comprised between 0.05% and 10% (w/v), preferably between 0.1% and 1%, more preferably between 0.2% and 0.3%.

According to step c) of process [2] of the invention, a hydroalcoholic solution (i) containing a zein and a basic amino acid is mixed with a hydroalcoholic solution (ii) comprising a fat-soluble BAC; a mixture comprising a zein, a basic amino acid and a fat-soluble BAC is thus formed in a hydroalcoholic medium. The fat-soluble BAC:zein ratio by weight present in the mixture formed in said step c) can vary within a wide range; nevertheless, in a particular embodiment, the ratio by weight between the fat-soluble BAC and zein [fat-soluble BAC:zein] is comprised between 1:0.5 and 1:70, preferably between 1:5 and 1:50, more preferably between 1:10 and 1:30.

In step d) of process [2] of the invention, water is added on the mixture formed in step c) in an amount sufficient for the formation of the nanoparticles of the invention. Although the amount of water to be added can vary within a wide range, in a particular embodiment, water is added in an amount sufficient for the final proportion of alcohol in the medium to be comprised between 10% and 60% (w/v), preferably between 15% and 30%, more preferably approximately 25%.

In another aspect, the invention relates to a process for producing nanoparticles comprising a zein matrix, a basic amino acid and a water-soluble biologically active compound (nanoparticles of the invention loaded with a water-soluble BAC), hereinafter "process [3] of the invention", which comprises:

a) preparing a hydroalcoholic solution (i) containing a zein and a basic amino acid;

b) preparing an aqueous solution comprising a water-soluble BAC and, optionally, a second basic amino acid, and diluting it with an alcohol to obtain a hydroalcoholic solution (ii) comprising a water-soluble BAC and, optionally, a second basic amino acid;

c) mixing said hydroalcoholic solution (i) containing a zein and a basic amino acid with said hydroalcoholic solution (ii) comprising a water-soluble BAC and, optionally, a second basic amino acid;

d) optionally adding a surfactant to the mixture resulting from step c); and e) adding water to the mixture resulting from step c) or from step d).

The hydroalcoholic solution (i) containing a zein and a basic amino acid used in step a) of process [3] of the invention contains water and an alcohol, typically ethanol; in a particular embodiment, said hydroalcoholic solution comprises between 25% and 75% (w/v) alcohol, preferably between 30% and 60%, more preferably approximately 50%. Said hydroalcoholic solution (i) is prepared by mixing its components in the suitable amounts.

The amount of zein which said hydroalcoholic solution (i) containing a zein and a basic amino acid used in step a) of process [3] of the invention can contain can vary within a wide range; nevertheless, in a particular embodiment, the amount of zein contained in said hydroalcoholic solution (i) is comprised between 0.1% and 10% (w/v), preferably between 0.2% and 2.5%, more preferably between 0.5% and 1%.

The amount of basic amino acid which said hydroalcoholic solution (i) containing a zein and a basic amino acid used in step a) of process [3] of the invention can contain can vary within a wide range. Said amount will generally be expressed according to the amount of zein to be dissolved. Thus, although the ratio by weight between the basic amino acid and the zein [basic amino acid:zein] present in said hydroalcoholic solution (i) can vary extensively, in a particular embodiment, said basic amino acid:zein ratio by weight is comprised between 1:0.01 and 1:50, typically between 1:0.5 and 1:25, preferably, between 1:1 and 1:20, more preferably between 1:5 and 1:15; in a specific embodiment, the basic amino acid:zein ratio by weight is approximately 1:6.7.

The hydroalcoholic solution (ii) comprising a water-soluble BAC generated in step b) of process [3] of the invention can be obtained by dissolving or solubilizing said water-soluble BAC in water, optionally, in the presence of a second basic amino acid, and then diluting the aqueous solution obtained with an alcohol (e.g., ethanol). Therefore, said hydroalcoholic solution (ii) comprising a water-soluble BAC and, optionally, a second basic amino acid generated in step b) of process [3] of the invention contains water and an alcohol, typically ethanol; in a particular embodiment, said hydroalcoholic solution (ii) comprises between 25% and 75% (w/v) alcohol, preferably between 30% and 60%, more preferably approximately 50%.

The aqueous solution resulting from dissolving the water-soluble BAC in water and, optionally, in the presence of said second basic amino acid, contains in a particular embodiment, said water-soluble BAC and water; and, in another particular embodiment, said water-soluble BAC, said basic amino acid and water. Said second basic amino acid will generally be present in said aqueous solution [and, consequently in said hydroalcoholic solution (ii)] when its presence is necessary to dissolve the water-soluble BAC since the solubilization of some water-soluble BACs, e.g., folic acid, can be facilitated by using an aqueous solution basified with said basic amino acid; in such cases, the ratio by weight between said water-soluble BAC and said second basic amino acid in said basified aqueous solution can be comprised between 1:0.25 and 1:5, preferably between 1:0.5 and 1:2, more preferably between 1:0.8 and 1:1.8; subsequently, as has been mentioned above, this aqueous solution is diluted in a hydroalcoholic medium (e.g., in ethanol) to obtain said hydroalcoholic solution (ii), as has been mentioned above, which comprises between 25% and 75% (w/v) alcohol, preferably between 30% and 60%, more preferably approximately 50%.

Process [3] of the invention contemplates the possibility of using 2 different basic amino acids. Thus, in a particular embodiment, the basic amino acid used in the preparation of the hydroalcoholic solution (i) containing zein and a basic amino acid (first basic amino acid) and the one used in the preparation of the hydroalcoholic solution (ii) comprising a water-soluble BAC and (in this case) a second basic amino acid (second basic amino acid) is the same and is selected from the group consisting of arginine, lysine, histidine, and mixtures thereof, preferably, lysine.

The amount of water-soluble BAC which said hydroalcoholic solution (ii) can contain can vary within a wide range; nevertheless, in a particular embodiment, the amount of water-soluble BAC contained in said hydroalcoholic solution (ii) is comprised between 0.01% and 10% (w/v), preferably between 0.05% and 5%, more preferably between 0.1% and 1%.

According to step c) of process [3] of the invention, a hydroalcoholic solution (i) containing a zein and a basic amino acid is mixed with a hydroalcoholic solution (ii) comprising a water-soluble BAC and, optionally, a second basic amino acid; a mixture comprising a zein, a basic amino acid, a water-soluble BAC and, optionally, a second basic amino acid (which, as has been mentioned above, can be the same as the basic amino acid contained in said hydroalcoholic solution (i)) is thus formed. The water-soluble BAC:zein ratio by weight present in the mixture formed in step c) can vary within a wide range; nevertheless, in a particular embodiment, the ratio by weight between the water-soluble BAC and the zein [water-soluble BAC:zein] in said mixture formed in step c) is comprised between 1:0.2 and 1:50, preferably between 1:1 and 1:15, more preferably between 1:6 and 1:12.

In the optional step d) of process [3] of the invention, a surfactant is added to the mixture resulting from step c). Without wishing to be bound by any theory, the surfactant is believed to facilitate the encapsulation of the water-soluble BAC in the nanoparticles since it allows moving the water-soluble BAC closed to the lipophilic polymer matrix (zein), thus facilitating its entrapment at the time of inducing coacervation. In a particular embodiment, said surfactant is a non-ionic surfactant, such as a polysorbate, for example, an ester derived from a fatty acid (e.g., oleic acid) and from a polyethyoxylated sorbitan such as the one marketed with the name Tween® 80. The surfactant:water-soluble BAC ratio by weight present in the mixture formed in step d) can vary within a wide range; nevertheless, in a particular embodiment, the ratio by weight between the surfactant and the water-soluble BAC [surfactant:water-soluble BAC] is comprised between 1:10 and 1:50, preferably between 1:15 and 1:45, more preferably between 1:20 and 1:30.

Finally, in step e) of process [3] of the invention water is added on the mixture formed in step c) or in step d) in an amount sufficient for the formation of the nanoparticles of the invention. Although the amount of water to be added can vary within a wide range, in a particular embodiment, water is added in an amount sufficient for the final proportion of alcohol in the medium to be comprised between 10% and 60% (w/v), preferably between 15% and 30%, more preferably approximately 25%.

Virtually any zein can be used to put said processes [1], [2] and [3] of the invention into practice; nevertheless, in a particular embodiment, said zein is a zein from corn, such as the zein supplied by Sigma-Aldrich (product number Z 3625).

Although alcohols of a very diverse nature can be used, in a particular and preferred embodiment of this invention, the hydroalcoholic solution used in processes [1], [2] and [3] of the invention is ethanol.

Virtually any basic amino acid can be used to put said processes [1], [2] and [3] of the invention into practice; nevertheless, in a particular embodiment, said basic amino acid is selected from the group consisting of arginine, lysine, histidine and mixtures thereof, preferably, lysine. Said basic amino acid, which can be inside or outside the nanoparticles of the invention plays a fundamentally technological role since:

it facilitates the dissolution of the components before the formation of the nanoparticles; it specifically contributes to the dissolution of zein since the latter, in the presence of the basic amino acid, can be dissolved in a hydroalcoholic solution with a lower proportion of alcohol (e.g., 50%) with respect to its dissolution in the absence of said amino acid, and it furthermore facilitates the dissolution of BACs, particularly of some water-soluble BACs, specifically of acidic water-soluble BACs (e.g., folic acid);

it maintains the suitable pH after the production of said nanoparticles on both sides of the nanoparticles (inside and outside); and it allows obtaining nanoparticles with a surface charge which is negative and far from ±10 mV, which hinders the aggregation thereof.

Therefore, the basic amino acid has a very important role in the production of the nanoparticles, both loaded with BACs and unloaded, of the invention.

The nanoparticles of the invention are characterized by having an average particle size less than 1 μm, typically comprised between 1 and 999 nm, preferably between 10 and 900 nm, more preferably between 50 and 500 nm, even more preferably between 100 and 450 nm, still more preferably between 140 and 400 nm. The nanoparticles of the invention advantageously have a particle size of about 200 nm approximately, for the purpose of preventing the alteration of organoleptic properties (texture on the palate), which is particularly suitable when they are used in the food field.

The nanoparticles of the invention, both those which are loaded with a BAC and those which are not (empty nanoparticles), can incorporate in their formulation an antioxidant, e.g., ascorbic acid (vitamin C), etc., for the purpose of increasing their stability against temperature and oxidation. In this case, said antioxidant could be introduced co-encapsulated with the BAC (where appropriate) or in the envelope of the nanoparticles of the invention; to that end, said processes [1], [2] and [3] of the invention will be suitably adapted to incorporate the antioxidant in the formulation of the nanoparticles, for example, by adding the antioxidant to the aqueous solution containing said BAC and, optionally, said second basic amino acid.

In a particular embodiment, the BAC is folic acid and the antioxidant is ascorbic acid which seems to act by protecting folic acid from the degradation by ultraviolet radiation, pH change, heat, oxygen, etc., further providing the nutritional contribution of the ascorbic acid itself. Said antioxidant could be introduced co-encapsulated with the BAC or in the envelope of the nanoparticles of the invention.

Additionally, if desired, process [1] of the invention as well as processes [2] and [3] of the invention can include one or more additional stabilization steps for stabilizing the nanoparticles obtained by means of using different treatments.

In a particular embodiment, said stabilization treatment comprises subjecting the suspension containing the formed nanoparticles of the invention, both those which are loaded with a BAC and those which do not have it, to a high-pressure treatment, for example at a pressure comprised between 100 and 800 MPa, typically between 350 and 600 MPa. In a particular embodiment, said treatment comprises subjecting the suspension of nanoparticles to cycles of 3 to 5 minutes at a pressure of 100 MPa to 800 MPa, typically between 350 and 600 MPa; in fact, a pressure of 400 MPa provides good results.

In another particular embodiment, said stabilization treatment comprises subjecting the suspension containing the formed nanoparticles of the invention, both those which are loaded with a BAC and those which do not have it, to a UHT (Ultra High Temperature) treatment, for example, at a temperature comprised between 130° C. and 140° C. for 2 to 5 seconds, followed by a rapid cooling.

Likewise, if desired, process [1] of the invention as well as processes [2] and [3] of the invention can include a drying step for drying the suspension containing the formed nanoparticles for the purpose of obtaining the nanoparticles of the invention, both those which are loaded with a BAC and those which do not have it, in the form of a powder. This form of presentation of said nanoparticles contributes to their stability and is furthermore particularly useful for their possible application in solid foods, such as flour, bread, pastry products, cereals, milk powder, etc., as well as in cosmetic and/or pharmaceutical products. Virtually any conventional method or technique suitable for drying suspensions containing nanoparticles can be used to perform this drying step; nevertheless, in a particular embodiment, the suspension containing nanoparticles is dried by means of drying by aspiration or spraying (spray drying) or by means of lyophilization. This treatment is generally carried out by adding to the suspension of the nanoparticles a suitable protective agent for said nanoparticles, such as a saccharide, for example, lactose, trehalose, mannitol, sucrose, maltodextrin, glucose, sorbitol, maltose, etc., and mixtures thereof. Said protective agent protects the nanoparticles of the invention both against thermal degradation and against oxidation during the drying process.

The zein:saccharide ratio by weight can vary within a wide range; nevertheless, in a particular embodiment, the zein:saccharide ratio by weight is comprised between 1:1 and 1:4, preferably about 1:2.

Likewise, in a particular embodiment, the solution containing the saccharide could further contain an antioxidant agent, such as ascorbic acid (vitamin C), etc.; in this case, the zein:saccharide:protective agent, for example, vitamin C, ratio by weight could be 1:0.75-2.5:0.25-1.5, preferably 1:1.5:0.5.

The nanoparticles of the invention obtained according to process [1] of the invention, i.e., the nanoparticles comprising a zein matrix and a basic amino acid produced by means of process [1] are an additional aspect of the present invention.

Likewise, the loaded nanoparticles of the invention obtained according to processes [2] or [3] of the invention, i.e., the nanoparticles comprising a zein matrix and a basic amino acid loaded with a fat-soluble or water-soluble BAC are an additional aspect of the present invention.

Applications

The nanoparticles of the invention have the capacity to encapsulate a BAC, e.g., a water-soluble BAC or a fat-soluble BAC. They can furthermore be used as technological additives, for example, favoring a uniform dispersion of the BAC in a medium in which it is not soluble, etc.

In a particular embodiment, the nanoparticles of the invention enable the encapsulation of a BAC and its incorporation in pharmaceutical, cosmetic and food compositions, since other ingredients which are not natural polymers (preventing the toxicity associated with synthetic polymers) and food-grade ingredients are not used in their preparation and in the final product (nanoparticles). Said nanoparticles protect the BAC from their degradation against external agents (light, pH changes, oxidation, etc.).

The nanoparticles of the invention can be resuspended in an aqueous medium, protecting the BAC from degradation in solution. It can furthermore be presented in the form of a dry powder, keeping the BAC stable and enabling its storage for long time periods (particularly for the incorporation thereof in solid food preparations).

Additionally, the nanoparticles of the invention are also suitable for the preparation of cosmetic and pharmaceutical compositions for topical use.

Therefore, in another aspect, the invention relates to a composition, hereinafter "composition of the invention", comprising at least one nanoparticle of the invention and a carrier acceptable in food, pharmacy or cosmetic; in a particular embodiment, said composition of the invention comprises a plurality of nanoparticles of the invention. In a particular embodiment, said nanoparticle of the invention is a nanoparticle comprising a zein matrix and a basic amino acid; in another particular embodiment, said nanoparticle of the invention is a loaded nanoparticle of the invention, i.e., a nanoparticle comprising a zein matrix and a basic amino acid, and a BAC with nutritional, therapeutic and/or cosmetic activity, and a pharmaceutically or cosmetically acceptable carrier or a carrier suitable for food.

Said nanoparticles of the invention have an average particle size less than 1 μm, typically comprised between 1 and 999 nm, preferably between 10 and 900 nm, more preferably between 50 and 500 nm, even more preferably between 100 and 450 nm, still more preferably between 140 and 400 nm. The nanoparticles of the invention advantageously have a particle size of about 200 nm approximately for the purpose of preventing the alteration of organoleptic properties (texture on the palate), which is particularly suitable when they are used in the food field.

In a particular embodiment, said BAC is selected from the group consisting of amino acids, antimicrobial agents, flavoring agents, preservatives, sweeteners, steroids, drugs, hormones, lipids, peptides, polynucleotides, polysaccharides, proteins, proteoglycans, flavors, vitamins, and mixtures thereof.

In a particular embodiment, said BAC is a fat-soluble BAC. Non-limiting illustrative examples of fat-soluble BACs include vitamins, for example of the A, D, E, K families and their derivatives, phospholipids, carotenoids (carotenes, lycopene, lutein, capsanthin, zeaxanthin, etc.), omega-3 fatty acids (e.g. DHA, EPA, etc.), amino acids (e.g., iso-leucine, leucine, methionine, phenylanine, tryptophan, and valine), phytostanols and phytosterols (e.g. sitosterol, campesterol, stigmasterol, etc.), polyphenols (e.g. quercetin, rutin, resveratrol, kaempferol, myricetin, isorhamnetin, etc.) and their derivatives.

In another particular embodiment, said BAC is a water-soluble BAC, preferably, a water-soluble BAC acid. Non-limiting illustrative examples of water-soluble BACs include vitamins, for example, vitamins of the B or C families and their derivatives, salts or esters; hyaluronic acid, chondroitin sulfate, thioctic acid, the salts or esters thereof, etc. In a particular embodiment, said water-soluble BAC is selected from the group consisting of folic acid, 4-aminobenzoic acid, niacin, pantothenic acid, thiamine monophosphate, thiamine pyrophosphate, thiamine triphosphate, ascorbic acid, pteroylpolyglutamic acids (folic acid derivatives: folate polyglutamates; polyglutamate folates), folinic acid, nicotinic acid, hyaluronic acid, thioctic acid, p-coumaric acid, caffeic acid, their food-grade or pharmaceutically or cosmetically acceptable derivatives, esters or salts, and mixtures thereof.

In a particular embodiment, the composition of the invention is a pharmaceutical composition suitable for its topical administration; to that end, said composition comprises a pharmaceutically acceptable carrier comprising one or more excipients suitable for the topical administration thereof, for example, in the form of gel, ointment, cream, etc. Information about excipients suitable for the formulation of pharmaceutical compositions intended for their topical administration as well as about the production of said pharmaceutical compositions can be found in the book "Tratado de Farmacia Galénica", by C. Fauli i Trillo, 10 Edition, 1993, Luzán 5, S. A. de Ediciones. The dose to be administered of nanoparticles of the invention can vary within a wide range, for example, between approximately 0.5 (g/cm² of area to be treated) and approximately 2 (g/cm² of area to be treated), of a composition of the invention containing between 0.1% and 30% of nanoparticles of the invention, preferably between 0.5% and 5%.

In another particular embodiment, the composition of the invention is a cosmetic composition suitable for its topical administration; to that end, said composition comprises a cosmetically acceptable carrier comprising one or more excipients suitable for the topical administration thereof, for example, in the form of gel, cream, shampoo, lotion, etc. Information about excipients suitable for the formulation of cosmetic compositions intended for their topical administration as well as about the production of said cosmetic compositions can be found in the book "Manual de Cosmetología", by Octavio Díez Sales, 1$^{st}$ Edition, 1998, Editorial Videocinco, S. A.

In another particular embodiment, the composition of the invention is a food composition, such as a solid, liquid or semi-solid food preparation.

In a particular embodiment, the composition of the invention comprises:
  zein between 15% and 45% by weight;
  a basic amino acid between 1% and 4% by weight;
  quercetin or resveratrol between 0.5% and 5% by weight; and
  a saccharide between 45% and 80% by weight,
wherein all the proportions are by weight with respect to the total weight of the composition.

In another particular embodiment, the composition of the invention comprises:
  zein between 15% and 45% by weight;
  a basic amino acid between 4% and 10% by weight;
  optionally, polysorbate (e.g., tween 80) between 0.05% and 0.5% by weight;
  folic acid between 0.5% and 5% by weight;
  a saccharide between 45% and 80% by weight; and
wherein all the proportions are by weight with respect to the total weight of the composition.

Alternatively, the composition of the invention can be incorporated in a food product. Therefore, in another aspect, the invention relates to a food product comprising a composition of the invention. Said food product can be in liquid, semi-solid or solid form. Advantageously, for the purpose of preventing or minimizing the total or partial dissolution of the nanoparticles of the invention and thus contributing to their stability, said food product has an acidic pH, i.e., less than 7, preferably equal to or less than 6, more preferably equal to or less than 5. Illustrative examples of food products which can be enriched or fortified with the composition of the invention include milks and its derivatives (yoghurts, cheeses, curds, etc.), juices, jams, bread and pastry products, fermented meat, sauces, etc. Likewise, the composition of the invention can be incorporated in a product for animal food, for example, in feeds.

EXAMPLES

The following examples describe the production of nanozein particles and a basic amino acid, such as lysine, which can incorporate a biologically active compound [BAC] therein, specifically resveratrol, quercetin or folic acid. Said nanoparticles are capable of protecting said BAC from the degradations it may experience in the food due to changes in the pH, light, oxidation, etc.

General Process for Producing Empty Zein Nanoparticles

The general process for producing zein nanoparticles comprises the dissolution of said protein, zein (Sigma-Aldrich-product number Z 3625), in a hydroalcoholic solution such as for example, a 50% (w/v) ethanol solution together with a particular amount of lysine (Sigma-Aldrich), followed by the addition, under magnetic stirring and a constant flow, of a particular volume of water to give rise to the formation of the nanoparticles with the appearance of a yellowish milky suspension.

Physicochemical Characterization of the Nanoparticles

The different studies necessary for achieving a complete physicochemical characterization of the nanoparticles are described below.

The size and the surface charge of the nanoparticles were determined within the physicochemical tests. The first of said parameters (size) was obtained by photon correlation spectroscopy using a Zetasizer Nano Z-S (Malvern Instruments/Optilas, Spain). The second of said parameters (surface charge) was determined through the measurement of the zeta potential using a Zeta Potential Analyzer (Brookhaven Instruments Corporation, New York, USA).

The yield of the process of the formation of nanoparticles was calculated through the quantification of the remaining free zein after obtaining the nanoparticles, collected in the supernatants obtained upon centrifuging the formulation (17, 000×g, 20 minutes). For the quantification, the supernatants were diluted in ethanol until obtaining a concentration of the alcohol of 75% (w/v), the latter being the same medium in which the standards of the calibration curve were prepared.

The amount of protein (zein) forming particles in the formulation was estimated as the difference between the initial amount added and the amount quantified in the supernatants collected during the purification step. The yield was estimated as:

$$\text{Yield (\%)} = \frac{\text{Total mg of Zein} - \text{mg of Zein in Supernatant}}{\text{Total mg of Zein}} \cdot 100 \quad [\text{Eq. 1}]$$

In addition, to confirm the results obtained by the difference between the total and the zein content of the supernatant, a quantification study of the pellet obtained after the centrifugation was conducted. In this case, a hydroalcoholic solution of 75% (w/v) ethanol was used to break the particles, the latter being the same medium used to prepare the calibration curve. Thus, in this case the yield was estimated as:

$$\text{Yield (\%)} = \frac{\text{mg of Zein in pellet}}{\text{Total mg of Zein}} \cdot 100 \quad [\text{Eq. 2}]$$

Furthermore, to confirm the validity of the quantification method and to verify that there is no matrix effect, known volumes of formulation without centrifugation were taken and diluted until obtaining a concentration of ethanol of 75%. It was thus possible to quantify the total zein present in the formulation and compare it with the amount of zein initially added, finding in all the cases deviations lower than 5%.

To perform the different calculations a calibration curve between 90 and 1,200 µg/mL was used ($R^2$=0.999; LOD=43 µg/mL; LOQ=143 µg/mL).

All the quantifications were carried out by means of UV spectrophotometry at 278 nm (Agilent 8453, UV-visible spectroscopy system).

The morphology of the nanoparticles was observed by scanning electron microscopy (Zeiss, DSM 940A Germany). To that end, the nanoparticles were covered with a layer of molecular gold of about 9 nm (Emitech K550 Equipment, Sputter-Coater, United Kingdom) and the photographs were taken with a Zeiss DMS 940 A microscope (United States).

General Process for Producing Zein Nanoparticles Containing Quercetin or Resveratrol The general process for producing zein nanoparticles loaded with quercetin or resveratrol comprises the dissolution of the protein (zein) in a hydroalcoholic medium (50% ethanol (w/v)) together with a particular amount of lysine followed by the addition, under magnetic stirring, of a particular volume of a dilution with water of a previously prepared alcoholic solution of said antioxidant (quercetin or resveratrol). After incubating the mixture for a few minutes, the last step consists of adding a particular volume of water to give rise to the formation of the nanoparticles with the appearance of a yellowish milky suspension.

Then, if desired, after a homogenization of 3 minutes by means of stirring, a particular volume of a solution of a saccharide (lactose, trehalose, mannitol, glucose, sorbitol, maltodextrin, maltose, etc.) is added without stopping the stirring. Finally, the suspension is sprayed in a spray dryer (Büchi Mini Spray Drier B-191, Büchi Labortechnik AG, Switzerland) under the following conditions:

Air inlet temperature: 70-110° C.
Air outlet temperature: 30-90° C.
Air pressure: 2-10 bar [$2\times10^5$-$10\times10^5$ Pa]
Sample pumping rate: 2-9 mL/min
Aspiration (Aspirator): 30-100%
Air flow: 200-900 L/h Optionally, after adding the saccharide, the formulations can be dried by means of lyophilization instead of by means of aspiration or spraying (spray drying).

Determination of the Amount of Quercetin or Resveratrol Associated with the Zein Particles The amount of quercetin or resveratrol associated with the nanoparticles was quantified by means of high-performance liquid chromatography (HPLC) according to the process described by Lacopini (Lacopini et al., J Food Comp Anal 2008; 21:589-598), although with several variations. The analysis was carried out in a chromatograph model 1100 series LC (Agilent, Waldbornn, Germany) coupled to a diode-array UV detection system.

For the analysis of fresh samples (before their drying), the supernatants obtained after the nanoparticle purification process [by filtering a particular volume of the formulation through Vivaspin® 300,000 MWCO dialysis tubes (VIVASPIN 2, Sartorius Stedim Biotech, Germany)], were diluted until obtaining a hydroalcoholic solution with an ethanol content of 75% (w/v). The pellet was in turn also dissolved in 75% (w/v) ethanol to break the particles and maintain the zein as well as the BAC (quercetin or resveratrol) and the amino acid in solution and thus carry out the quantification thereof. The sum of the BAC content found in both fractions (supernatant and pellet) matched at all times the total added initially. Furthermore, it was also possible to quantify the total amount of BAC by dissolving a particular volume of the formulation in 75% ethanol (w/v). This study allowed confirming that the differences between the amount of BAC added and that obtained by quantification through the described chromatographic method were less than 10% in all the cases.

In addition, for the preparation of the powder samples (dried formulations), approximately 15 mg of the formulation of nanoparticles were taken and resuspended in ethanol. The supernatant obtained after filtering a particular volume of the suspension through Vivaspin® 300,000 MWCO dialysis tubes (VIVASPIN 2, Sartorius Stedim Biotech, Germany) was diluted with distilled water to a concentration of ethanol of 75% (w/v). The pellet was dissolved in a particular volume of 75% ethanol (w/v). Furthermore, the total BAC contained in the 15 mg of powder was also quantified by directly dissolving them in 75% (w/v) ethanol.

The samples were analyzed using an Alltech C18 Alltima™ column (5 µm, 150 mm×2.1 mm) heated at 40° C. with a compatible Gemini® C18 AJ0-7596 precolumn and a mixture of water/methanol/glacial acetic acid in a gradient (see Table 1) as a mobile phase pumped at a flow of 0.25 mL/min.

The detection was performed at 360 nm for quercetin and at 306 nm for resveratrol. The sample injection volume was 10 µL. The retention time of said compounds is 24.2±0.2 minutes in the case of quercetin and 22.8±0.5 minutes in the case of resveratrol.

TABLE 1

| Gradient conditions for the mobile phase (A: water, B: methanol, C: glacial acetic acid) | | | |
| --- | --- | --- | --- |
| Time (min) | A (%) | B (%) | C (%) |
| 0 | 80 | 15 | 5 |
| 15 | 70 | 25 | 5 |
| 20 | 10 | 85 | 5 |
| 30 | 10 | 85 | 5 |
| 35 | 80 | 15 | 5 |
| 40 | 80 | 15 | 5 |

Before quantifying the samples, different calibration lines of concentrations between 1 and 100 µg/mL in a hydroalcoholic medium (75% ethanol) were prepared, obtaining precision and accuracy results less than 5%.

Finally, the amount of quercetin or resveratrol associated with the nanoparticles [encapsulation efficiency (E.E.)] was calculated as the difference between the amount of the BAC added initially and the amount thereof quantified in the supernatants.

$$E.E.\ (\%) = \frac{\text{Total mg of } BAC - \text{mg of } BAC \text{ in Supernatant}}{\text{Total mg of } BAC} \cdot 100$$

General Process for Producing Zein Nanoparticles Containing Folic Acid

The general process for producing zein nanoparticles loaded with folic acid comprises the dissolution of the protein (zein) in a hydroalcoholic medium (50% (w/v) ethanol) together with a particular amount of lysine followed by the addition, under magnetic stirring, of a particular volume of an alcoholic dilution of a previously prepared aqueous solution of said vitamin. After incubating the mixture for a few minutes, the last step consists of adding a particular volume of water to give rise to the formation of the nanoparticles with the appearance of a yellowish milky suspension.

Then, if desired, after a homogenization of 3 minutes by means of stirring, a particular volume of solution of a saccharide (lactose, trehalose, mannitol, glucose, sorbitol, maltodextrin, maltose, etc.) is added without stopping the stirring. Finally, the suspension is sprayed in a spray dryer (Büchi Mini Spray Drier B-191, Büchi Labortechnik AG, Switzerland) under the following conditions:

Air inlet temperature: 70-130° C.

Air outlet temperature: 30-90° C.

Air pressure: 2-10 bar [$2 \times 10^5$-$10 \times 10^5$ Pa]

Sample pumping rate: 2-9 mL/min

Aspiration (Aspirator): 30-100%

Air flow: 200-900 L/h

Optionally, after adding the saccharide, the formulations can be dried by means of lyophilization instead of by means of aspiration or spraying (spray drying).

Determination of the Amount of Folic Acid Associated with the Zein Particles

The amount of folic acid associated with the nanoparticles was quantified by means of high-performance liquid chromatography (HPLC) according to the process described by Faye [Faye Russell, L., Quantitative Determination of Water-Soluble Vitamins. In *Food Analysis by HPLC*, Nollet, L. M. L. (Ed.), Marcel Dekker, Inc., New York, Second Edition, Chapter 10 (2000) pp. 444-445]. The analysis was carried out in a chromatograph model 1100 series LC (Agilent, Waldbornn, Germany) coupled to a diode-array UV detection system. The data were analyzed in a Hewlett-Packard computer by means of the Chem-Station G2171 software. For the separation of folic acid, an Alltech C18 Alltima™ column (5 μm, 150 mm×2.1 mm) heated at 40° C., with a compatible Gemini® C18 AJ0-7596 precolumn, was used. The mobile phase was formed by a mixture of $H_3PO_4$ (33 mM, pH 2.3)/acetonitrile in a gradient (Table 2) and was pumped at a flow of 0.25 mL/min. The detection was performed at 290 nm. The sample injection volume was 10 μL. The retention time of folic acid is 22.6±0.5 minutes.

TABLE 2

Gradient conditions for the mobile phase (A: $H_3PO_4$ 33 mM, B: Acetonitrile).

| Time (min) | A (%) | B (%) |
| --- | --- | --- |
| 0 | 95.0 | 5.0 |
| 8 | 95.0 | 5.0 |
| 33 | 82.5 | 17.5 |
| 45 | 95.0 | 5.0 |

Before quantifying the samples, different calibration lines of concentrations between 2 and 400 μg/mL were prepared, obtaining precision and accuracy results greater than 95%, with the confirmation of the fact that the presence of zein and/or amino acids in the solution did not interfere in the correct quantification of folic acid.

For the analysis of fresh samples (before their drying), the supernatants obtained after filtering a particular volume of the formulation through Vivaspin® 300,000 MWCO dialysis tubes (VIVASPIN 2, Sartorius Stedim Biotech, Germany) were quantified. The pellet was in turn dissolved in 0.05 M NaOH to break the particles and maintain the zein as well as the folic acid and the amino acid in solution and thus carry out the quantification thereof. The sum of folic acid content found in both fractions (supernatant and pellet) matched at all times the total added initially. Furthermore, it was also possible to quantify the total amount of folic acid by dissolving 1 mL of the formulation in 1 mL of 0.05 M NaOH. This study allowed confirming that the differences between the amount of folic acid added and that obtained by quantification through the described chromatographic method are less than 10% in all the cases.

In addition, for quantifying the powder samples, 15 mg of nanoparticles were taken, resuspended in 2 mL of water and centrifuged, then proceeding in the same manner as with the fresh samples.

Pharmacokinetic Studies. Bioavailability of Folic Acid Encapsulated in Zein Nanoparticles The pharmacokinetic studies were carried out according to the rules of the ethics committee of the Institution as well as the European laws on experimental animals (86/609/EU). To that end, 20 male Wistar rats with an average weight of 200 g were subjected to normal conditions of light-darkness (12 hours-12 hours), and during the week before the study they were fed with a folic acid-deficient feed (Folic Acid Deficient Diet. TD. 95247. Harlan, USA) and water. Twelve hours before the administration of the formulations, the rats were isolated in metabolic cages without access to food, but with free access to drinking water.

The animals were divided into 4 treatment groups (5 rats per group). Only 1 mL of PBS (Phosphate Buffer, pH 7.4) was orally administered to the first of the group. The two following groups were treated with single oral doses of 1 mg/kg (200 μg/rat) of folic acid (Aditio, Panreac Quimica, Barcelona, Spain) incorporated in zein nanoparticles, or in free form (not encapsulated) dissolved in water. 1 mL of each of the different formulations dispersed in water was administered through a gastroesophageal cannula. Finally, the same dose of free folic acid (1 mg/kg) dissolved in phosphate buffer (PBS) (0.5 mL) was intravenously administered to the fourth group in the saphenous vein. Before the administration of the formulations, blood was extracted from the tail saphenous vein for the purpose of checking the baseline level of the vitamin in each rat. After the administration, a volume of blood of approximately 500 μL was extracted at different times using serum-separating tubes (SARSTEDT Microtube 1.1 mL Z-Gel). In all the cases, to prevent the pain of the rats, the extraction was carried out after anesthetizing the animal with inhalational anesthesia (isoflurane:oxygen), checking their vital signs at all times.

The blood volume was subsequently replaced by intraperitoneally administering 500 μL of physiological saline previously heated to the temperature of the animal. During this period, the condition of the animals (mobility, aggressiveness, allergic reactions and temperature) was examined, no significant changes being observed.

Pretreatment and Quantification of the Folic Acid of the Serum Samples

The quantification of folic acid in the serum samples, obtained after centrifuging the tubes with blood (6,000 rpm, 20 minutes, 20° C.), was carried out by means of an enzyme immunoassay technique. To that end, an Elisa Kit (Diagnostic automation, INC. Calabasas, Calif. USA) approved by the FDA for the quantitative determination of folic acid in foods, was used. The serum samples were quantified without prior treatment and following the manufacturer's specifications.

In view of the fact that the kit is designed for use in foods, a series of prior studies was conducted for the purpose of confirming its capacity to quantify the vitamin in serum samples. Said studies consisted of making an exhaustive comparison between the results obtained by means of the kit and those obtained by the high-performance liquid chromatography described in previous sections, with the following prior preparation process: variable amounts (0-300 μL) of folic acid dissolved in a 50 mM sodium tetraborate solution prepared in 1% (w/v) sodium ascorbate were added to 50 μL of serum. The resulting solution was taken to a final volume of 350 μL (1:7 dilution of the serum) with the 50 mM sodium tetraborate solution. Each mixture was taken to boiling for 30 minutes and subsequently cooled to 2° C. and preserved overnight at said temperature.

After centrifuging the resulting samples at 20,000 rpm for 20 minutes and filtering them through a 20 μm filter, their folic acid content was quantified by means of high-performance liquid chromatography using the method described above. In this case, and due to the low serum concentration of the vitamin, the standard additions technique was used to minimize the errors in the quantification and remove any interference of the matrix. This method of extraction and quantification by HPLC was validated according to the criteria established by the FDA.

In all the studied cases, the differences in the serum folic acid concentrations found by both methods were less than 10%. Therefore, the enzyme immunoassay technique was chosen to quantify all the samples, since it requires a smaller amount of serum for the analysis thereof and is a simpler and quicker technique, the limit of detection of which (2 ng/mL) is much lower than that of the chromatographic technique.

Example 1

Preparation and Characterization of Empty Zein Nanoparticles

Yield of the Obtaining Process. Influence of the Amount of Lysine Incorporated in the Formulation on the Physicochemical Characteristics of the Nanoparticles 60 mg of zein (Sigma-Aldrich) together with 10 mg of lysine (Sigma-Aldrich) were dissolved in 8.8 mL of a 50% (w/v) ethanol solution. Subsequently, 8.8 mL of water were added on this solution under magnetic stirring and a constant flow to form the nanoparticles. This process was performed in triplicate.

FIGS. 1 (A and B) shows the images obtained by transmission electron microscopy of the zein particles obtained by this method.

For the purpose of knowing the influence of lysine and the percentage of ethanol of the initial hydroalcoholic solution on the physicochemical characteristics of the nanoparticles, 3 new formulations were prepared by varying these parameters: (i) one of them without lysine, (ii) another one with lysine and the initial hydroalcoholic solution prepared in 75% (w/v) ethanol instead of 50% (w/v), and (iii) the third one was also prepared in 75% (w/v) ethanol and without lysine.

Table 3 summarizes the main physicochemical parameters of the resulting nanoparticles.

TABLE 3

Physicochemical characteristics of the zein nanoparticles (mean ± SD, n = 6) in the presence of different amounts of lysine and percentages of ethanol in which zein is dissolved before the formation of the nanoparticles

| Lysine:zein ratio by weight | Percentage of ethanol | Size (nm) | PDI[a] | Zeta potential (mV) | Yield[b] (%) |
|---|---|---|---|---|---|
| 0 (*) | 50 | 150 ± 4 | 0.11 ± 0.03 | −7.2 ± 3.6 | — |
| 1:6 | 50 | 142 ± 4 | 0.12 ± 0.09 | −37.8 ± 1.6 | 94.7 ± 1.1 |
| 0 | 75 | 203 ± 2 | 0.09 ± 0.01 | −8.9 ± 7.6 | 94.7 ± 2.4 |
| 1:6 | 75 | 164 ± 2 | 0.07 ± 0.01 | −46.0 ± 1.5 | 98.5 ± 1.6 |

(*) Partially soluble
[a]PDI: polydispersion
[b]Yield: Percentage of zein transformed into nanoparticles [Eq. 1]

The statistical studies conducted (non-parametric test of independent samples: Kruskal-Wallis) revealed the existence of statistically significant evidence to affirm that the presence of lysine leads to an increase of the surface charge thereof. The formulations prepared with large initial amounts of ethanol (75% (w/v)) showed greater sizes and yields with respect to those obtained from an initial 50% (w/v) ethanol solution, there being no significant differences in the surface charge thereof.

The surface charge found in the samples which did not contain lysine was very close to zero, which means that said particles had a greater tendency for agglomeration. However, in the presence of lysine, the surface charge is high enough to prevent said phenomenon.

Thus, for the encapsulation of the BAC the formulations obtained from a hydroalcoholic solution containing 50% (w/v) ethanol and in the presence of lysine were chosen since this prevents the aggregation of the nanoparticles, it makes them versatile for the encapsulation of both fat-soluble and water-soluble BACs and, furthermore, a significant saving in the use of the reagent is achieved.

Example 2

Preparation and Characterization of Zein Nanoparticles Containing Resveratrol

Influence of the Lysine and Resveratrol Content on the Encapsulation Efficiency

Different hydroalcoholic solutions were prepared, all of them containing 60 mg of zein and variable amounts of lysine (0, 5, 10 or 20 mg) in a final volume of 8.8 mL of 50% ethanol.

In addition, 47 mg of resveratrol were dissolved in 15 mL of ethanol and then diluted to 24 mL with water.

Variable volumes of the resveratrol solution (1, 2 or 3 mL) were subsequently added on the different zein solutions prepared. After 5 minutes of incubation, 8.8 mL of water were added on the mixture under magnetic stirring and a constant flow. This process was performed in triplicate for each type of formulation.

Table 4 shows the physicochemical characteristics of the nanoparticles obtained in each case.

TABLE 4

Physicochemical characteristics of the zein nanoparticles (initially dissolved in 50% ethanol (w/v)) with variable amounts of lysine (mean ± SD, n = 3) with encapsulated resveratrol. The ratio by weight between resveratrol and zein is 1:16

| Lysine:zein ratio by weight | Size (nm) | PDI | Zeta potential (mV) | Resveratrol content (μg R/mg NP) | Encapsulation efficiency (%) |
|---|---|---|---|---|---|
| 0 | 149 ± 1 | 0.08 ± 0.02 | 23.3 ± 0.7 | 56.3 ± 3.6 | 83.7 ± 1.9 |
| 1:12 | 154 ± 1 | 0.08 ± 0.03 | −30.5 ± 0.9 | 59.0 ± 3.1 | 91.4 ± 1.9 |
| 1:6 | 148 ± 1 | 0.08 ± 0.02 | −45.2 ± 3.0 | 54.6 ± 2.3 | 85.2 ± 1.3 |
| 1:3 | 167 ± 2 | 0.07 ± 0.02 | −44.2 ± 1.2 | 56.7 ± 3.0 | 88.1 ± 1.9 |

R: Resveratrol;
NP: Nanoparticle

The results obtained show that the presence of lysine does not significantly affect the encapsulation efficiency. Thus, taking into account that said amino acid modifies the surface charge of the particles and reduces the possibility of their aggregation and, furthermore, that it increases the yield of the formation of particles, the formulation containing the amino acid incorporated therein was chosen to continue the study.

Table 5 shows the physicochemical characteristics of the nanoparticles obtained by varying the resveratrol content when the amount of lysine is constant.

TABLE 5

Physicochemical characteristics of the zein nanoparticles (initially dissolved in 50% ethanol w/v) with variable amounts of resveratrol (mean ± SD, n = 3). The ratio by weight between lysine and zein is 1:6

| Resveratrol:zein ratio by weight | Size (nm) | PDI | Zeta potential (mV) | Resveratrol content (μg R/mg NP) | Encapsulation efficiency (%) | μg R/mg formulation |
|---|---|---|---|---|---|---|
| 1:10.4 | 162 ± 1 | 0.10 ± 0.02 | −48.0 ± 0.7 | 70.9 ± 6.4 | 70.4 ± 1.9 | 76.1 |
| 1:16 | 148 ± 1 | 0.08 ± 0.02 | −45.2 ± 3.0 | 54.6 ± 2.3 | 85.2 ± 1.3 | 51.1 |
| 1:31.4 | 171 ± 3 | 0.06 ± 0.02 | −42.4 ± 2.8 | 28.9 ± 1.8 | 92.4 ± 3.8 | 26.4 |

R: Resveratrol;
NP: Nanoparticle

The results obtained reveal that as the amount of resveratrol added to the formulation increases, the encapsulation efficiency decreases but the amount of bioactive substance encapsulated inside the particles increases.

Example 3

Preparation and Characterization of Zein Nanoparticles Containing Resveratrol Dried by Aspiration Spray Drying 126 mg of zein were dissolved together with 21 mg of lysine in 14 mL of 50% (w/v) ethanol.

In addition, 60 mg of resveratrol were dissolved in 10 mL of ethanol and 1.4 mL of that solution were subsequently collected and taken to a final volume of 2.8 mL with water.

1.1 mL of the diluted resveratrol solution were then added on the zein solution and the mixture was left to incubate for 5 minutes. After that time, 15 mL of water were added to the mixture under magnetic stirring and a constant flow.

Finally, 260 mg of maltodextrin were added to the mixture before drying it by means of using the spray dryer. The conditions of the process were:
Air inlet temperature: 110° C.
Air outlet temperature: 70° C.
Air pressure: 6 bar [6×10$^5$ Pa]
Sample pumping rate: 4.5 mL/min
Aspiration: 94%
Air flow: 700 L/h Table 6 summarizes the physicochemical characteristics of the resulting formulation.

TABLE 6

Physicochemical characteristics of the zein nanoparticles with lysine and resveratrol (R) (mean ± SD, n = 3), dried by means of the spray-drying technique, using maltodextrin as an adjuvant of the process. The ratio by weight between lysine and zein is 1:6. The ratio by weight between the saccharide (maltodextrin) and zein is 2:1

| Size (nm) | PDI | Zeta potential (mV) | μg R/mg formulation |
|---|---|---|---|
| 245 ± 6 | 0.24 ± 0.01 | −30.3 ± 0.3 | 9.4 ± 0.8 |

The amount encapsulated per mg of nanoparticles and the encapsulation efficiency are not modified by spray drying.

Figure 2:
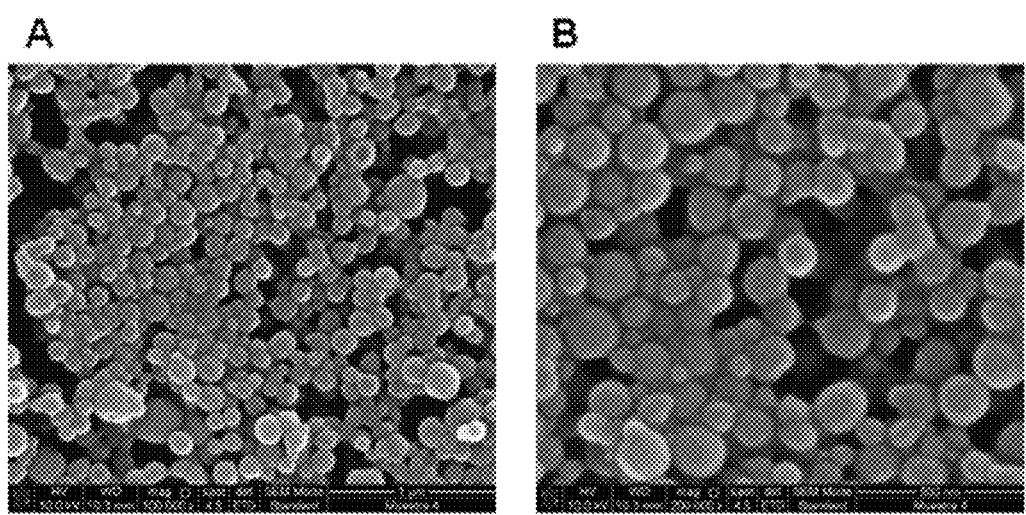
FIG. 2 shows the scanning electron microscopy (SEM) micrographs of nanoparticles comprising a zein matrix and lysine containing resveratrol. The images correspond to the powder formulation after being washed to remove the protective saccharide.

FIG. 2 shows the images obtained by scanning electron microscopy of the zein particles containing resveratrol.

In addition, the same experiments were carried out applying the high-pressure technique (150 MPa in a cycle of 5 minutes and 400 MPa in a cycle of 5 minutes) after the formation of the nanoparticles, before their passage through the spray dryer. The encapsulation results obtained were similar to those obtained without said treatment.

Example 4

Preparation and Characterization of Zein Nanoparticles Containing Quercetin

Influence of the Lysine and Quercetin Content on the Encapsulation Efficiency

Different solutions were prepared, all of them containing 60 mg of zein and 10 mg of lysine in a final volume of 8.8 mL of 50% ethanol.

In addition, 150 mg of quercetin were dissolved in 50 mL of ethanol and subsequently diluted by taking 31 mL of the previous solution and taking them to a final volume of 50 mL with water.

Variable volumes of the quercetin solution (0.5-3 mL) were subsequently added on the different zein solutions prepared. After 5 minutes of incubation, 8.8 mL of water were added on the mixture under magnetic stirring and a constant flow. This process was performed in triplicate for each type of formulation.

Figure 3:
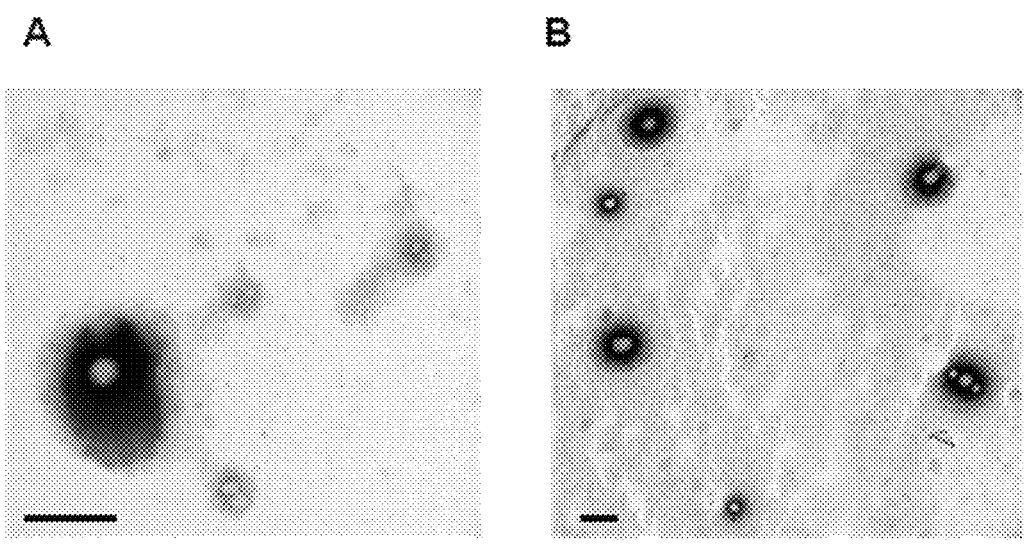
FIG. 3 shows the transmission electron microscopy (TEM) images of nanoparticles comprising a zein matrix and lysine containing quercetin. A) 25,000× (the black bar located in the bottom left margin of the images corresponds to a reference of 150 nm). B) 10,000× (the black bar located in the bottom left margin of the images corresponds to a reference of 150 nm).

FIG. 3 shows the images obtained by transmission electron microscopy of the zein particles with encapsulated quercetin obtained by this method. Table 7 shows the physicochemical characteristics obtained in each case.

TABLE 7

Physicochemical characteristics of the zein nanoparticles with lysine and variable amounts of quercetin (Q) (mean ± SD, n = 6). The ratio by weight between lysine and zein is 1:5.5

| Quercetin: zein ratio by weight | Size (nm) | PDI | Zeta potential (mV) | Quercetin content µg Q/ mg NP | Encapsulation efficiency (%) |
|---|---|---|---|---|---|
| 1:64 | 147 ± 1 | 0.22 ± 0.01 | −60.2 ± 1.4 | 16.1 ± 1.0 | 93.2 ± 8.0 |
| 1:30 | 161 ± 4 | 0.13 ± 0.03 | −57.1 ± 1.2 | 29.1 ± 1.8 | 85.6 ± 1.3 |
| 1:20 | 161 ± 1 | 0.05 ± 0.01 | −48.3 ± 3.2 | 38.5 ± 1.3 | 76.7 ± 2.5 |
| 1:16 | 165 ± 2 | 0.04 ± 0.03 | −46.8 ± 2.4 | 48.7 ± 1.1 | 77.9 ± 1.8 |
| 1:11 | 167 ± 2 | 0.06 ± 0.01 | −45.1 ± 2.4 | 59.7 ± 2.6 | 64.6 ± 2.7 |

NP: Nanoparticle

Figure 4:
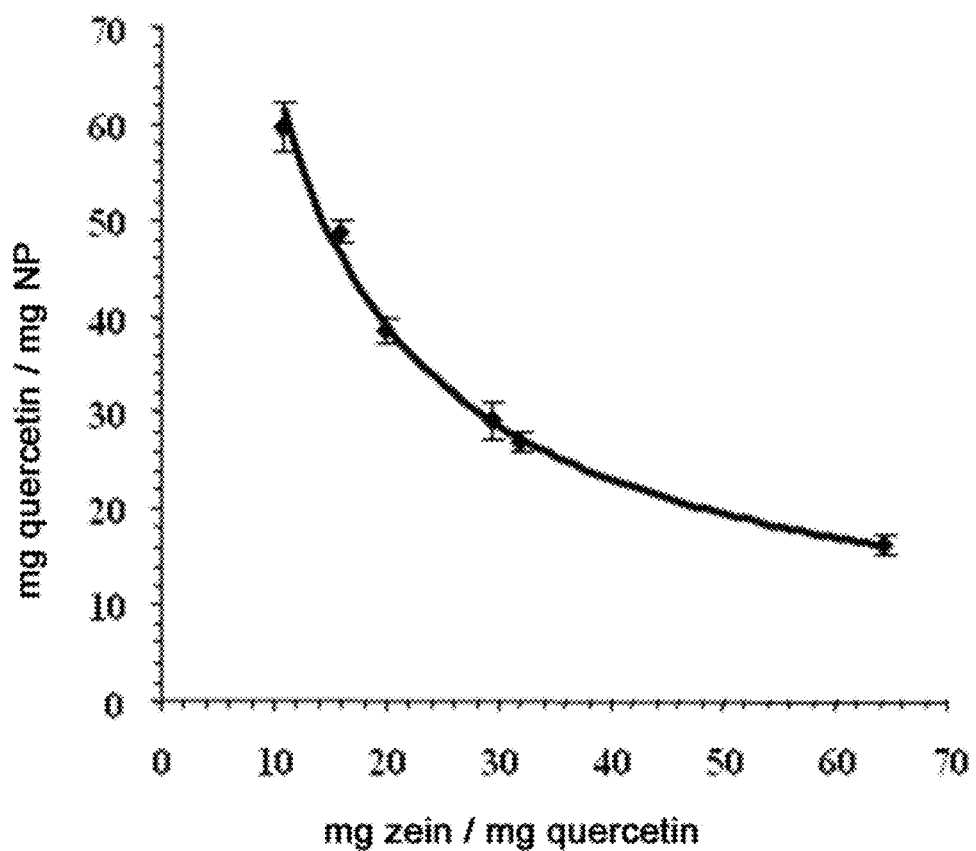
FIG. 4 shows the amount of quercetin encapsulated in nanoparticles (NP) comprising a zein matrix and lysine, as a function of the amount of quercetin initially incorporated in the formulation.

The statistical studies conducted (non-parametric test of independent samples: Kruskal-Wallis) revealed the existence of statistically significant evidence to consider that there were differences in the physicochemical characteristics of the different formulations. In view of the results obtained, it can be considered that as the amount of quercetin added to the formulation increases, the encapsulation efficiency decreases and the amount of encapsulated BAC (quercetin) increases potentially (FIG. 4), considering the following mathematical expression:

$$y=369.92 \cdot x^{-0.7526}; R^2=0.9955 \quad [\text{Eq. 3}]$$

wherein y corresponds to the amount of encapsulated quercetin (µg Q/mg NP), and x corresponds to the initial ratio between quercetin and zein (mg zein/mg quercetin).

With respect to the sizes and potentials, no statistically significant differences were found between the different samples analyzed.

In addition, an attempt was made to known the influence of the greater or smaller presence of lysine in the formulation on the physicochemical characteristics of the nanoparticles, therefore the same study was conducted, keeping the initial amount of quercetin constant and varying the amount of amino acid added in this case.

Thus, different zein solutions containing variable amounts of lysine (0 to 20 mg) were prepared. The amount of the quercetin solution described above which was added to the formulation was 3 mL in all the cases so the quercetin:zein ratio by weight was 1:11.

Table 8 shows the physicochemical characterization results obtained in each case.

TABLE 8

Physicochemical characteristics of the zein nanoparticles with quercetin and variable amounts of lysine (mean ± SD, n = 6). The ratio by weight between quercetin and zein is 1:11

| Lysine: zein ratio by weight | Size (nm) | PDI | Zeta potential (mV) | Quercetin content µg Q/ mg NP | Encapsulation efficiency (%) |
|---|---|---|---|---|---|
| 0 | 164 ± 1 | 0.10 ± 0.02 | 17.8 ± 0.9 | 72.4 ± 2.8 | 82.5 ± 2.7 |
| 1:11 | 167 ± 2 | 0.06 ± 0.01 | −45.1 ± 2.4 | 74.7 ± 8.2 | 78.9 ± 8.4 |
| 1:5.5 | 158 ± 1 | 0.06 ± 0.05 | −44.4 ± 1.0 | 59.7 ± 2.6 | 64.6 ± 2.7 |
| 1:4 | 164 ± 1 | 0.04 ± 0.03 | −45.6 ± 0.4 | 61.6 ± 6.4 | 66.4 ± 6.9 |
| 1:3 | 181 ± 3 | 0.05 ± 0.03 | −41.9 ± 2.2 | 58.1 ± 1.9 | 64.2 ± 6.9 |

The results obtained show that, in the case of quercetin, when amounts greater than 10 mg are added to the initial zein solution, the encapsulation efficiency is reduced by approximately 20% with respect to the formulations containing smaller amounts of lysine, probably due to the fact that said amounts of amino acid induce a partial oxidation of the active ingredient. However, no statistically significant differences were found between the encapsulation efficiencies of the samples without lysine and those containing about 5 mg of the latter in the formulation. Therefore, this was the formulation selected to continue with the drying studies.

Example 5

Preparation and Characterization of Zein Nanoparticles Containing Quercetin Dried by Spray Drying 602 mg of zein together with 51 mg of lysine were dissolved in 80 mL of 50% (w/v) ethanol.

In addition, 250 mg of quercetin were dissolved in 50 mL of ethanol and 20 mL of that solution were subsequently collected and taken to a final volume of 32 mL with water.

20 mL of the diluted quercetin solution were then added on the zein solution and the mixture was left to incubate for 5 minutes. After that time, 80 mL of water were added to the mixture under magnetic stirring and a constant flow.

Finally, 1,209 mg of mannitol were added to the mixture before drying it by means of using the spray dryer. The conditions of the process were:

Air inlet temperature: 90° C.
Air outlet temperature: 45° C.
Air pressure: 6 bar [6×10⁵ Pa]
Sample pumping rate: 4.5 mL/min
Aspiration: 100%
Air flow: 600 L/h Table 9 summarizes the physicochemical characteristics of the resulting formulation.

TABLE 9

Physicochemical characteristics of the zein nanoparticles with lysine and quercetin (Q) (mean ± SD, n = 3), dried by means of the spray-drying technique, using mannitol as an adjuvant of the process. The ratio by weight between lysine and zein is 1:11. The ratio by weight between the saccharide (mannitol) and the protein is 2:1

| Size (nm) | PDI | Zeta potential (mV) | Yield (% in mass) | µg Q/mg formulation |
|---|---|---|---|---|
| 412 ± 14 | 0.10 ± 0.06 | −28.9 ± 2.2 | 50.6 | 22.2 ± 2.0 |

The amount encapsulated per mg of nanoparticles and the encapsulation efficiency are not modified by spray drying.

Figure 5:
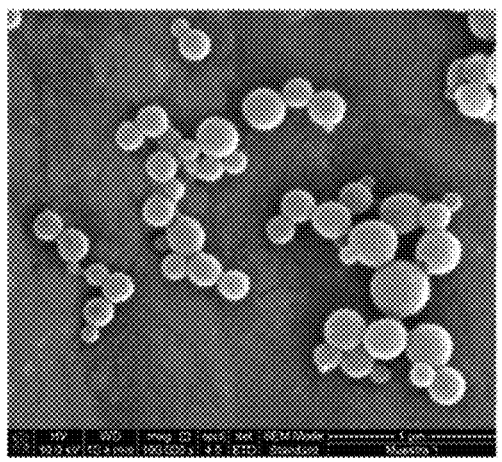
FIG. 5 shows the Scanning electron microscopy (SEM) micrographs of nanoparticles comprising a zein matrix and lysine containing quercetin. The images correspond to the powder formulation after being washed to remove the protective saccharide.
Figure 5:
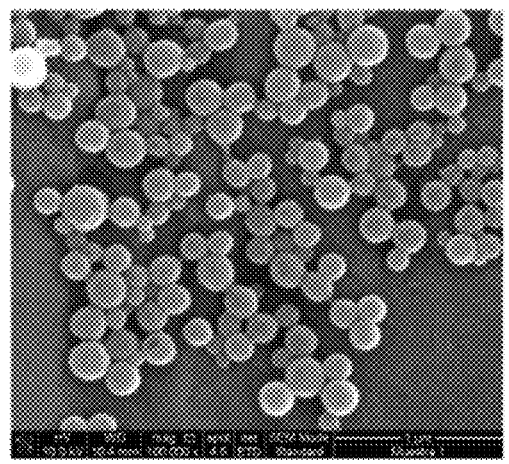

FIG. 5 shows the images obtained by scanning electron microscopy of the zein particles containing quercetin.

The same study was conducted using maltodextrin instead of mannitol as an adjuvant, obtaining greater encapsulation efficiencies since maltodextrin acts, furthermore, by coating the nanoparticles and encapsulating part of the quercetin remaining outside them.

In addition, the same experiments were carried out by applying the high-pressure technique (150 MPa in a cycle of 5 minutes, 400 MPa in a cycle of 5 minutes and 800 MPa in a cycle of 5 minutes) after the formation of the particles, before their passage through the spray dryer. The encapsulation results obtained were similar to those obtained without said treatment.

Example 6

Preparation and Characterization of Zein Nanoparticles Containing Folic Acid 121 mg of zein together with 18 mg of lysine were dissolved in 14 mL of 50% (w/v) ethanol.

In addition, 303 mg of folic acid together with 402 mg of lysine were dissolved in 50 mL of water and subsequently diluted by half with ethanol.

5 mL of the diluted folic acid solution were then added on the zein solution and the mixture was left to incubate for 5 minutes. After that time, 0.6 mL of Tween® 80 (polysorbate) were added to the mixture and the mixture was left to incubate for another 5 minutes. 15 mL of water were then added under magnetic stirring and a constant flow to form the nanoparticles.

Finally, 253 mg of lactose were added to the mixture before drying it by means of using the spray dryer. The conditions of the process were:

Air inlet temperature: 125° C.
Air outlet temperature: 90° C.
Air pressure: 6 bar [$6 \times 10^5$ Pa]
Sample pumping rate: 4.5 mL/min
Aspiration: 90%
Air flow: 750 L/h Table 10 summarizes the physicochemical characteristics of the resulting formulation.

TABLE 10

Physicochemical characteristics of the zein nanoparticles with lysine and folic acid (FA) (mean ± SD, n = 3), dried by means of the spray-drying technique, using lactose as an adjuvant of the process. The final ratio by weight between lysine and zein is 1:3. The ratio by weight between the saccharide (lactose) and zein is 2:1

| Size (nm) | PDI | Zeta potential (mV) | Encap-sulation efficiency (%) | Folic acid content µg FA/mg NP | µg FA/mg formulation |
|---|---|---|---|---|---|
| 369 ± 7 | 0.32 ± 0.06 | −49.0 ± 2.2 | 56.6 ± 1.5 | 70.7 ± 1.6 | 35.4 ± 0.1 |

FA: folic acid;
NP: Nanoparticle

In addition, a new formulation of zein nanoparticles containing folic acid was prepared, omitting in this case the step of the addition of surfactant. To that end, 1,270 mg of zein together with 200 mg of lysine were dissolved in 140 mL of 50% (w/v) ethanol. Another solution was furthermore prepared which contained 121 mg of folic acid and 200 mg of lysine in 25 mL of water, which was subsequently diluted by half with ethanol.

43 mL of the diluted folic acid solution were then added on the zein solution, leaving the mixture to incubate for 5 minutes. After that time, 150 mL of water were added under magnetic stirring and a constant flow to obtain the nanoparticles.

Finally, 2,415 mg of mannitol were added to the mixture before drying it by means of the spray drying technique. The conditions of the process were:

Air inlet temperature: 120° C.
Air outlet temperature: 80° C.
Air pressure: 6 bar [$6 \times 10^5$ Pa]
Sample pumping rate: 4.5 mL/min
Aspiration: 90%
Air flow: 750 L/h Table 11 summarizes the physicochemical characteristics of the resulting formulation.

TABLE 11

Physicochemical characteristics of the zein nanoparticles with lysine and folic acid (FA) (mean ± SD, n = 3), dried by means of the spray-drying technique, using mannitol as an adjuvant of the process. The final ratio by weight between lysine and zein is 1:3.5. The ratio by weight between the saccharide (mannitol) and zein is 2:1

| Size (nm) | PDI | Zeta potential (mV) | Folic acid content µg FA/mg NP | Encap-sulation efficiency (%) | µg FA/mg formulation |
|---|---|---|---|---|---|
| 181 ± 1 | 0.21 ± 0.06 | −55.3 ± 2.2 | 41.5 ± 2.5 | 50.8 ± 3.0 | 24.7 ± 1.6 |

FA: Folic acid;
NP: Nanoparticle

The resulting nanoparticles were easily resuspended and have smaller sizes than those obtained when the surfactant is used.

Example 7

Pharmacokinetic Study of Folic Acid Encapsulated in Zein Nanoparticles

Table 12 summarizes the main physicochemical characteristics of the nanoparticles tested in the pharmacokinetic study. Said nanoparticles were obtained following the process described in the second section of Example 6 (without surfactant).

TABLE 12

Physicochemical characteristics of the zein nanoparticles with folic acid (mean ± SD, n = 6) used in the pharmacokinetic studies

| Size (nm) | PDI | Zeta potential (mV) | Folic acid content µg FA/mg NP | Encapsulation efficiency (%) |
|---|---|---|---|---|
| 193 ± 3 | 0.16 ± 0.02 | −29.1 ± 3.3 | 53.6 ± 6.5 | 57.9 ± 6.0 |

FA: Folic acid;
NP: Nanoparticle

The pharmacokinetic study was divided into three phases. The first of them consisted of intravenously administering 1 mg/kg of folic acid dissolved in phosphate buffer; the second of them consisted of orally administering to the rats 1 mL of phosphate buffer (PBS) to a group of 5 male Wistar rats (the baseline levels of the vitamin over time were studied in this group of rats). Finally, the third phase consisted of orally administering 1 mg/kg of (i) folic acid dissolved in water, (ii) folic acid encapsulated in zein nanoparticles to groups of rats formed by 5 animals.

After the administration, a volume of blood of approximately 500 μL was extracted at different times (0, 1, 2, 3, 8 and 24 hours) and collected in serum-separating tubes, subsequently recovering the blood volume of the animal with an equivalent volume of saline by intraperitoneal route. The pharmacokinetic analysis of the data obtained after the administration of folic acid was conducted using the non-compartmental fit process of the pharmacokinetic fit program WiNNonlin 1.5 (Pharsight Corporation, Mountain View, United States).

Figure 6:
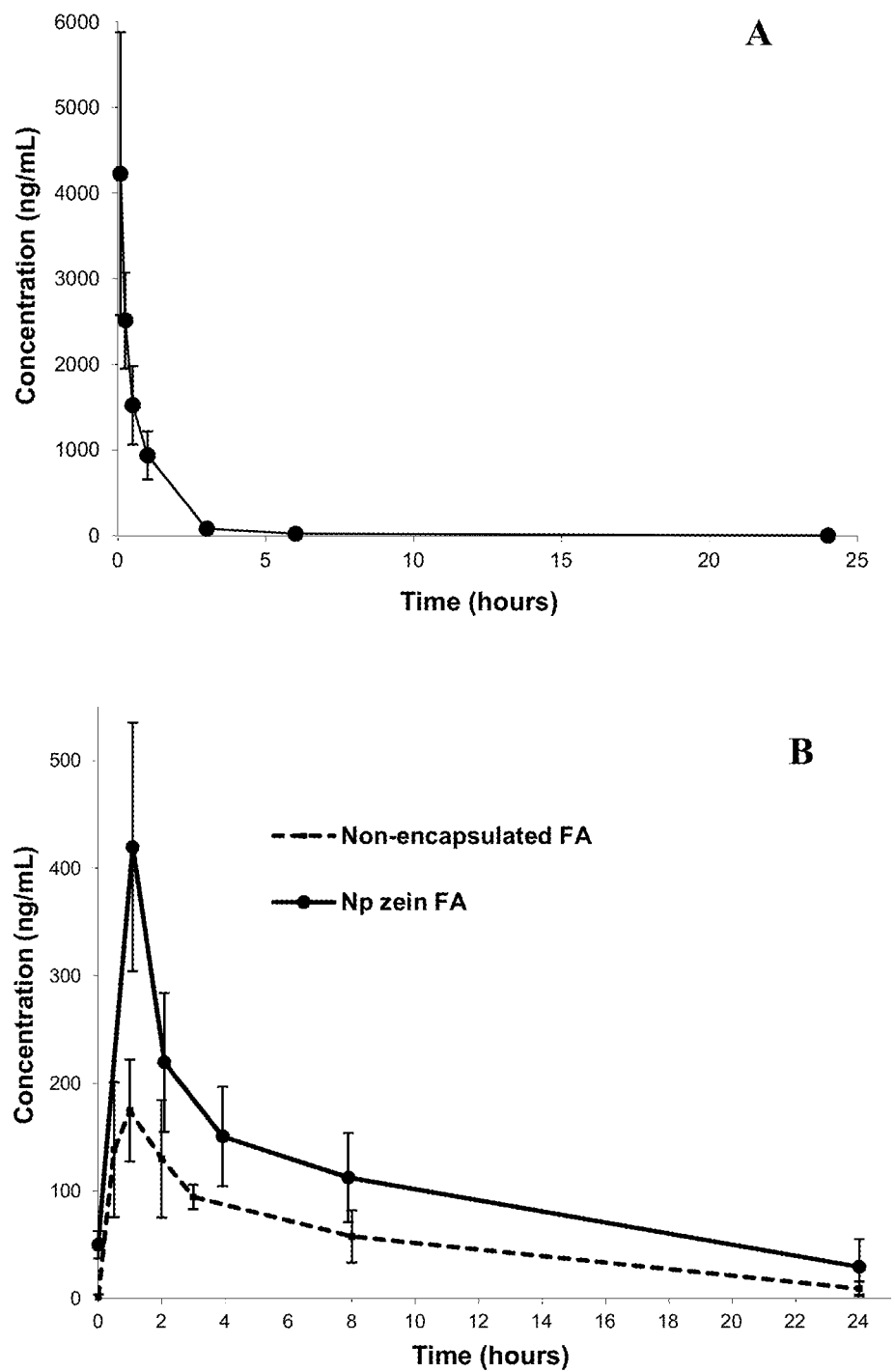
FIG. 6 shows the serum folic acid concentration (ng/mL) as a function of time, after the administration of the different formulations of the vitamin in laboratory animals. The results show the mean±standard deviation (n=5). (A) Intravenous route (i.v.), 1 mg/kg dose. (B) Oral route, 1 mg/kg dose: non-encapsulated folic acid dissolved in water (■); folic acid encapsulated in zein nanoparticles dispersed in water (●).

The results obtained (after subtracting the baseline values) are shown in FIG. 6. As can be observed, the i.v. administration of folic acid (FIG. 6A) shows a peak of serum concentration of the drug in the first sampling, followed by a drastic decrease of the serum levels. The profiles obtained when the vitamin is orally administered (FIG. 6B) are different, since the significantly lower concentration found appear at greater times and decrease in a more gradual manner. However, upon comparing the vitamin levels found after the oral administration of folic acid in its free form (without encapsulation) or encapsulated in zein nanoparticles, similar profiles of concentration over time were found, but both the maximum values and the areas under the curve were greater when the vitamin was administered in an encapsulated form.

Table 13 shows the values of the pharmacokinetic parameters obtained after conducting a non-compartmental analysis of the experimental data of the present study.

TABLE 13

Pharmacokinetic parameters of the different formulations tested
(mean ± SD, n = 5)

| Formulation | Tmax (min) | C max (ng/mL) | AUC (×10$^4$) (ng × min/mL) | MRT (min) | $F_R$ (%) |
|---|---|---|---|---|---|
| Non-encapsulated FA | 58.8 ± 36.0 | 191.3 ± 41.0 | 7.8 ± 1.5 | 383.8 ± 47.5 | 36.3 ± 7.2 |
| NP Zein FA | 61.8 ± 9.2 | 431.5 ± 133.8* | 15.2 ± 4.3* | 543.3 ± 48.0* | 70.8 ± 20.2* |
| FA IV route | — | 4227.1 ± 1651.5** | 21.5 ± 2.8** | 57.8 ± 15.5** | 100** |

*p < 0.05 vs. Non-encapsulated folic acid. Mann Whitney U test.
**p < 0.01 vs. Non-encapsulated folic acid. Mann Whitney U test.
AUC: area under the curve of serum concentration
$C_{max}$: maximum concentration
$T_{max}$: time at which the $C_{max}$ is reached
MRT: mean residence time
$F_R$: Relative bioavailability in percentage.
FA: Folic acid
NP: Nanoparticle
IV: Intravenous route As can be observed, the AUC values experience significant variations according to the type of sample administered. When the vitamin is encapsulated in zein nanoparticles, the AUC values are significantly greater than those found after administering free folic acid and, furthermore, they are maintained over time until 24 hours post-administration. Furthermore, it was observed that the mean residence time (MRT) of folic acid in plasma was also significantly greater than that obtained when the free vitamin was administered.

According to these results, the oral bioavailability of the zein nanoparticles with encapsulated folic acid was calculated, which was from 70% to 95% greater than the values obtained after the oral administration of free folic acid.

The invention claimed is:

1. A nanoparticle having an average particle size comprised between 1 and 999 nm comprising a zein matrix and a basic amino acid, wherein the nanoparticle is stable at a pH less than 7 and wherein the basic amino acid:zein ratio by weight is comprised between 1:0.01 and 1:50.

2. The nanoparticle according to claim 1, wherein said basic amino acid is selected from the group formed by arginine, lysine, histidine and mixtures thereof.

3. The nanoparticle according to claim 1, further comprising a biologically active compound.

4. The nanoparticle according to claim 3, wherein said biologically active compound is a fat-soluble biologically active compound.

5. The nanoparticle according to claim 4, wherein the fat-soluble biologically active compound is selected from the group formed by:
   a) a polyphenol;
   b) a vitamin of the family of vitamins A, D, E or K;
   c) a precursor or a derivative of a vitamin according to b);
   d) a phospholipid;
   e) a carotenoid;
   f) a fatty acid;
   g) a phytostanol or a phytosterol;
   h) a salt or an ester of any of the previous compounds a)-g); and
   i) combinations thereof.

6. The nanoparticle according to claim 5, wherein said fat-soluble biologically active compound is selected from the group formed by a flavonol, an anthocyanin, a phytoalexin, hydroxytyrosol, retinoic acid, retinal, retinol, calciferol, alpha-tocopherol, tocotrienol, phytomenadione, alpha-carotene, beta-carotene, lycopene, capsanthin, lutein, zeaxanthin, xanthophyll, EPA, DHA, linoleic acid, campesterol, stigmasterol, sitosterol, their food-grade or pharmaceutically or cosmetically acceptable derivatives, esters or salts, and mixtures thereof.

7. The nanoparticle according to claim 5, wherein said fat-soluble biologically active compound is selected from quercetin, resveratrol, their food-grade or pharmaceutically or cosmetically acceptable derivatives, esters or salts, and mixtures thereof.

8. The nanoparticle according to claim 3, wherein said biologically active compound is a water-soluble biologically active compound.

9. The nanoparticle according to claim 8, wherein the water-soluble biologically active compound is selected from the group formed by:
   a) a vitamin of the B or C family;
   b) a derivative of a vitamin according to a);
   c) a compound selected from hyaluronic acid, chondroitin sulfate and thioctic acid;
   d) a salt or an ester of any of the previous compounds a)-c); and
   e) combinations thereof.

10. The nanoparticle according to claim 9, wherein the water-soluble biologically active compound is selected from folic acid, its food-grade or pharmaceutically or cosmetically acceptable esters or salts, and mixtures thereof.

11. A composition comprising at least one nanoparticle as defined in claim 1, and a carrier acceptable in food, pharmacy or cosmetic.

12. The composition according to claim 11, selected from the group consisting of:
   a composition comprising:
      zein, between 15% and 45% by weight;
      a basic amino acid, between 1% and 4% by weight;
      quercetin or resveratrol, between 0.5% and 5% by weight; and
      a saccharide, between 45% and 80% by weight,
   wherein all the proportions are by weight with respect to the total weight of the composition; and
   a composition comprising:
      zein, between 15% and 45% by weight;
      a basic amino acid, between 4% and 10% by weight;
      optionally, a polysorbate, between 0.05% and 0.5% by weight;
      folic acid, between 0.5% and 5% by weight;
      a saccharide, between 45% and 80% by weight; and
   wherein all the proportions are by weight with respect to the total weight of the composition.

13. A food product comprising a composition as defined in claim 11.

14. A process for producing a nanoparticle comprising a zein matrix and a basic amino acid as defined in claim 1 which comprises:
   a) preparing a hydroalcoholic solution containing a zein and a basic amino acid; and
   b) adding water to the solution of step a).

15. The process according to claim 14, which further comprises:
   a) subjecting the suspension containing the zein nanoparticles formed to at least one hydrostatic pressure cycle at a pressure comprised between 100 and 800 MPa;
   b) if desired, drying the suspension containing the formed nanoparticles, wherein said drying is optionally carried out in the presence of a protective agent and/or an antioxidant agent.

16. A process for producing a nanoparticle comprising a zein matrix and a basic amino acid and a fat-soluble biologically active compound as defined in claim 4 which comprises:
   a) preparing a hydroalcoholic solution (i) containing a zein and a basic amino acid;
   b) preparing an alcoholic solution comprising a fat-soluble biologically active compound (BAC) and diluting it with water to obtain a hydroalcoholic solution (ii) comprising a fat-soluble BAC;
   c) mixing said hydroalcoholic solution (i) containing a zein and a basic amino acid with said hydroalcoholic solution (ii) comprising a fat-soluble BAC; and
   d) adding water to the mixture resulting from step c).

17. The process according to claim 16, which further comprises:
   a) subjecting the suspension containing the zein nanoparticles formed to at least one hydrostatic pressure cycle at a pressure comprised between 100 and 800 MPa;
   b) optionally drying the suspension containing the formed nanoparticles, wherein said drying is optionally carried out in the presence of a protective agent and/or an antioxidant agent.

18. A process for producing a nanoparticle comprising a zein matrix and a basic amino acid and a water-soluble biologically active compound as defined in claim 8 which comprises:
   a) preparing a hydroalcoholic solution (i) containing a zein and a basic amino acid;
   b) preparing an aqueous solution comprising a water-soluble biologically active compound (BAC) and, optionally, a second basic amino acid, and diluting it with an alcohol to obtain a hydroalcoholic solution (ii) comprising a water-soluble BAC and, optionally, a second basic amino acid;
   c) mixing said hydroalcoholic solution (i) containing a zein and a basic amino acid with said hydroalcoholic solution (ii) comprising a water-soluble BAC and, optionally, a second basic amino acid;
   d) optionally adding a surfactant to the mixture resulting from step c); and
   e) adding water to the mixture resulting from step c) or from step d).

19. The process according to claim 18, which further comprises:
   a) subjecting the suspension containing the zein nanoparticles formed to at least one hydrostatic pressure cycle at a pressure comprised between 100 and 800 MPa;
   b) optionally drying the suspension containing the formed nanoparticles, wherein said drying is optionally carried out in the presence of a protective agent and/or an antioxidant agent.

* * * * *